United States Patent [19]

Bourzat et al.

[11] Patent Number: 4,994,569

[45] Date of Patent: Feb. 19, 1991

[54] 5,6-DIHYDRO-4H-1,3-OXA(OR THIA)ZINE DERIVATIVES, THEIR PREPARATION AND COMPOSITIONS CONTAINING THEM

[75] Inventors: Jean-Dominique Bourzat, Vincennes; Claude Cotrel, Paris; Claude Guyon, Saint Maur des Fosses, all of France; Philippe Pitchen, Brentwood, Great Britain

[73] Assignee: Rhone-Poulenc Sante, Antony, France

[21] Appl. No.: 430,127

[22] Filed: Nov. 1, 1989

[30] Foreign Application Priority Data

Nov. 3, 1988 [FR] France ................. 88 14322

[51] Int. Cl.$^5$ ............... C07D 417/00; C07D 413/00; A61K 31/54
[52] U.S. Cl. ..................... 544/55; 544/96
[58] Field of Search ............... 514/71, 97; 544/298, 544/96, 88, 54

[56] References Cited

U.S. PATENT DOCUMENTS 3,876,770  4/1975  Wehrmeister ............. 514/228.8
4,151,272  4/1979  Singer ..................... 544/97

OTHER PUBLICATIONS

Iwakura et al., Chemical Abstracts, vol. 54, 1960, 11033a-f (note Chemical Abstract summary of reference cited below by same author).
Iwakura et al., Journal of Organic Chemistry, vol. 24, pp. 1992–1994, 1959.
Shiraki et al., Chemical Abstracts, vol. 107, 1987, p. 728, 176052k.

*Primary Examiner*—Shah, Mukund J.
*Assistant Examiner*—Deborah D. Carr

*Attorney, Agent, or Firm*—Morgan & Finnegan

[57] ABSTRACT

Compounds of formula:

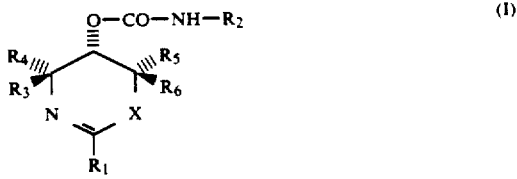

in which $R_1$ denotes 2-indolyl, 2-thienyl, 3-furyl, naphthyl, phenyl, or phenyl substituted with one or two halogen atoms, with alkoxy, alkyl, nitro, acylamino, alkylthio, acyl, trifluoromethoxy, morpholino, piperidino, amino, mono- or dialkylamino or, at the 3- and 4-positions, with methylenedioxy $R_2$ denotes phenyl or phenyl substituted with one or two halogen atoms, with one or two alkyl radicals, with alkoxy, nitro, trifluoromethyl or hydroxy or, at the 3- and 4-positions, with methylenedioxy and either X denotes oxygen and $R_3$ denotes phenyl $R_4$, $R_5$ and $R_6$ denote hydrogen, or $R_3$ and $R_4$ denote hydrogen, $R_5$ denotes hydrogen or methyl and $R_6$ denotes phenyl or one of $R_3$ and $R_4$ denotes methyl and the other hydrogen, $R_5$ denotes hydrogen and $R_6$ denotes phenyl, or X denotes sulphur, $R_3$ denotes phenyl and $R_4$, $R_5$ and $R_6$ denote hydrogen; the said acyl, alkyl and alkoxy radicals and acyl, alkyl and alkoxy portions containing 1 to 4 carbon atoms each in a straight or branched chain; and their salts are useful in the treatment and prevention of disorders in which therapy with a cholecystokinin antagonist is indicated.

28 Claims, No Drawings

5,6-DIHYDRO-4H-1,3-OXA(OR THIA)ZINE DERIVATIVES, THEIR PREPARATION AND COMPOSITIONS CONTAINING THEM

The present invention provides compounds of formula:

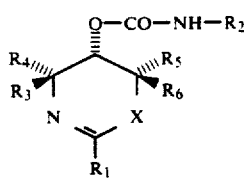
(I)

and their acid addition salts, in which:

$R_1$ denotes 2-indolyl, 2-thienyl, 3-furyl, naphthyl, phenyl or phenyl substituted by one or two halogen atoms, or by alkoxy, alkyl, nitro, acylamino, alkylthio, acyl, trifluoromethoxy, morpholino, piperidino, amino, monoalkylamino, or dialkylamino in which the alkyl groups are identical or different, or, at the 3- and 4-positions, by methylenedioxy, $R_2$ denotes phenyl or phenyl substituted by one or two halogen atoms, by one or two alkyl radicals, or by alkoxy, nitro, trifluoromethyl or hydroxy or, at the 3- and 4-positions by methylenedioxy, and either X denotes oxygen and $R_3$ denotes phenyl and $R_4$, $R_5$ and $R_6$ denote hydrogen or $R_3$ and $R_4$ denote hydrogen, $R_5$ denotes hydrogen or methyl and $R_6$ denotes phenyl, or one of $R_3$ and $R_4$ denotes methyl and the other hydrogen, $R_5$ denotes hydrogen and $R_6$ denotes phenyl, or X denotes sulphur, $R_3$ denotes phenyl and $R_4$, $R_5$ and $R_6$ denote hydrogen; the aforesaid alkyl, alkoxy and acyl radicals and alkyl, alkoxy and acyl portions containing 1 to 4 carbon atoms each in a straight or branched chain. The acid addition salts of the compounds of formula (I) may be formed with inorganic or organic acids.

In formula (I), the halogen atoms are preferably chlorine or fluorine atoms.

According to a feature of the invention, the compounds of formula (I), with the exception of those for which $R_2$ denotes phenyl substituted by hydroxy, may be prepared by the reaction of an isocyanate of formula

(II)

in which $R_2$ has the same meanings as in the formula (I), except phenyl substituted by hydroxy, on a compound of formula:

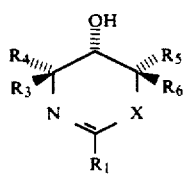
(III)

in which X, $R_1$, $R_3$, $R_4$, $R_5$ and $R_6$ have the same meanings as in the formula (I), or, when one of the substituents $R_3$ or $R_4$ denotes methyl and the other hydrogen, a mixture of these compounds.

This reaction is preferably performed in an inert solvent such as tetrahydrofuran, chloroform, methylene chloride or 1,2-dichloroethane, at a temperature between 20° C. and the boiling point of the solvent, optionally in the presence of a base such as an alkali metal hydride or 4-(dimethylamino)pyridine.

The isocyanates of the formula (II) are commercially available or may be obtained by application or adaptation of the methods described by RICHTER and ULRICH or DROBNICA, KRISTIAN and AUGUSTIN, Patai, "The chemistry of cyanates and their derivatives" Wiley, New York, p. 619-678 and 1003-1221, 1977.

The compounds of formula (III) for which $R_3$ denotes phenyl, $R_4$, $R_5$ and $R_6$ denote hydrogen, X denotes oxygen or sulphur, and $R_1$ has the same meanings as in formula (I), may be obtained by the cyclization of a derivative of formula

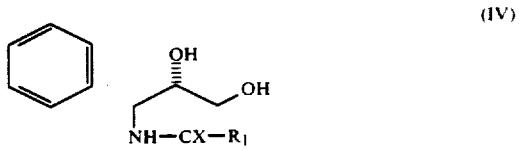
(IV)

in which $R_1$ and X have the same meanings as above.

For the compounds for which X denotes an oxygen atom, this reaction is generally performed by means of tosyl chloride, benzenesulphonyl chloride or mesyl chloride, either in the presence of a tertiary amine such as triethylamine, in a chlorinated solvent such as chloroform, methylene chloride or 1,2-dichloroethane, at a temperature of between 20° C. and 70° C., or in pyridine at a temperature of between 20° C. and 50° C.

For the compounds for which X denotes a sulphur atom, this reaction is generally performed in an inert solvent such as tetrahydrofuran, in the presence of triphenylphosphine and ethyl azodicarboxylate, at a temperature in the region of 20° C.

The derivative of formula (IV) for which X denotes an oxygen atom and $R_1$ denotes a phenyl radical may be prepared by the method described by T. SUAMI et al, Bull. Chem. Soc. Japan, 29, 417, 1956.

The other derivatives of formula (IV) may be obtained by reaction of a derivative of formula:

(V)

in which X and R have the same meanings as above and $R_7$ denotes a chlorine atom or an alkoxy, alkoxycarbonyloxy or N-imidazolyl radical, with the amine of formula:

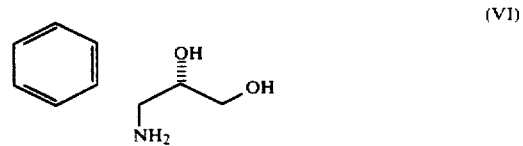
(VI)

This reaction is preferably performed in an inert solvent such as chloroform, methylene chloride, 1,2-dichloroethane, diethylether, tetrahydrofuran, toluene or a mixture of these solvents, at a temperature between 20° C. and the boiling point of the solvent, optionally in the presence of a tertiary amine such as triethylamine.

The derivatives of the formla (V) for which X denotes an oxygen atom may be obtained by the action, on the corresponding acid, of a saturated aliphatic alcohol such as methanol or ethanol, of a chlorinating agent such as oxalyl dichloride or thionyl chloride, of an alkyl chloroformate such as methyl or ethyl chloroformate or of carbonyldiimidazole.

The action of the aliphatic alcohol on the acid may be carried out in the said alcohol as solvent, in the presence of an inorganic acid such as sulphuric acid or hydrochloric acid, at the boiling point of the reaction medium.

The action of the chlorinating agent on the acid may be carried out in an inert solvent such as ethyl ether or chloroform, optionally in the presence of dimethylformamide at a temperature in the region of 20° C.

The action of the alkyl chloroformate on the acid may be carried out in an inert solvent such as chloroform or methylene chloride, at a temperature of between $-5°$ C. and 25° C., in the presence of a tertiary amine such as triethylamine.

The action of carbonyldiimidazole on the carboxylic acid may be carried out in an inert solvent such as tetrahydrofuran, dimethylformamide or dichloromethane, at a temperature in the region of 0° C.

The derivatives of formula (V) for which X denotes a sulphur atom may be prepared by application or adaptation of the method described by H. VIOLA and R. MAYER, Z. Chem., vol. 15, 348, 1975, from the corresponding dithiobenzoic acids.

The corresponding dithiobenzoic acids may be obtained by application or adaptation of the method described by D. F. AYCOCK and G. R. JURCH jr, J. Org. Chem., 44(4), 569, 1979.

The amine of formula (VI) may be prepared according to the method described by M. F. SAETONE et al., Il Farmaco, 31(3), 209, 1966.

The compounds of formula (III) for which $R_1$ denotes a 2-indolyl, 2-thienyl, 3-furyl, naphthyl or phenyl radical or a phenyl radical substituted with one or two halogen atoms, with an alkoxy, alkyl, nitro, acyl, or trifluoromethoxy radical or, at the 3- and 4-positions, with a methylenedioxy radical, X denotes an oxygen atom, and either $R_3$ and $R_4$ denote a hydrogen atom, $R_5$ denotes a hydrogen atom or a methyl radical and $R_6$ denotes a phenyl radical, or one of the substituents $R_3$ or $R_4$ denotes a methyl radical and the other a hydrogen atom, $R_5$ denotes a hydrogen atom and $R_6$ denotes a phenyl radical, or mixtures or these latter compounds, may be prepared by the action of m-chloroperbenzoic acid on a compound of formula:

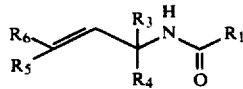

(VII)

in which $R_1$, $R_3$, $R_4$, $R_5$ and $R_6$ have the same meanings as above, followed by cyclization of the product obtained.

The action of m-chloroperbenzoic acid on the compound of formula (VII) is generally performed in a chlorinated solvent such as 1,2-dichloroethane, chloroform or methylene chloride, at a temperature in the region of 0° C. The cyclization is preferably performed by means of boron trifluoride etherate, at a temperature in the region of 20° C.

The compounds of formula (VII) may be prepared by application or adaptation of the methods described by PADWA et al, J. Org. Chem., 44(19), 3281, 1979 and Mc MANUS et al., J. Org. Chem., 43(22), 4288, 1978.

Preferably, a derivative of formula (V) in which X denotes an oxygen atom and $R_1$ and $R_7$ have the same meanings as above is reacted with an amine of formula:

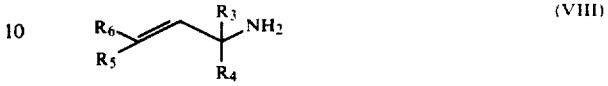

(VIII)

in which $R_3$, $R_4$, $R_5$ and $R_6$ have the same meanings as in the formula (VII).

This reaction is generally performed in a chlorinated solvent such as dichloromethane or chloroform, in the presence of a tertiary amine such as triethylamine, at a temperature of between 20° C. and 40° C.

The amines of formula (VIII) for which one of the substituents $R_3$ or $R_4$ denotes a methyl radical and the other a hydrogen atom, $R_5$ denotes a hydrogen atom and $R_6$ denotes a phenyl radical may be obtained by the process described by T. G. SCHENK et al., J. Am. Chem. Soc., 107(7), 2064, 1985.

The amine of formula (VIII) for which $R_3$ and $R_4$ denote a hydrogen atom, $R_5$ denotes a methyl radical and $R_6$ denotes a phenyl radical may be obtained by reduction of the corresponding nitrile. This reduction is generally performed by means of lithium aluminium hydride, preferably in diethyl ether, at a temperature of $-15°$ C.

The corresponding nitrile may be obtained by the method described by TEXIER et al., Synthesis, 884, 1979.

The compounds of formula (III) for which $R_1$ denotes a phenyl radical substituted with an amino, mono- or dialkylamino, acylamino, alkylthio, morpholino or piperidino radical, X denotes an oxygen atom, and either $R_3$ and $R_4$ denote a hydrogen atom, $R_5$ denotes a hydrogen atom or a methyl radical and $R_5$ denotes a phenyl radical, or one of the substituents $R_3$ or $R_4$ denotes a methyl radical and the other a hydrogen atom, $R_5$ denotes a hydrogen atom and $R_6$ denotes a phenyl radical, or mixtures of these latter compounds, may be prepared by the cyclization of a compound of formula:

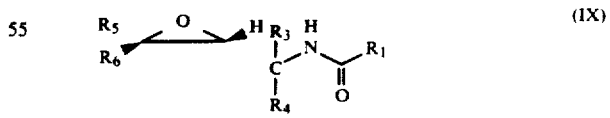

(IX)

in which $R_1$, $R_3$, $R_4$, $R_5$ and $R_6$ have the meanings stated above.

This cyclization is generally accomplished by means of boron trifluoride etherate, in an inert solvent such as 1,2-dichloroethane, chloroform or methylene chloride or diethyl ether, at a temperature in the region of 20° C.

The compounds of formula (IX) may be obtained by hydrolysis of an amide of formula:

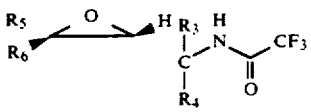

in which $R_3$, $R_4$, $R_5$ and $R_6$ have the same meanings as in the formula (IX), followed by the action of the product thereby obtained and isolated, in the form of a solution in an inert solvent such as dichloromethane, on a derivative of formula (V) in which $R_1$ denotes a phenyl radical substituted with an amino, mono- or dialkylamino, acylamino, alkylthio, morpholino or piperidino radical and $R_7$ denotes an N-imidazolyl radical.

The hydrolysis may be carried out by means of an alkali metal hydroxide such as potassium hydroxide, in an aqueous medium, at a temperature in the region of 20° C.

The action of the hydrolysed product, dissolved in an inert solvent, on a derivative of the formula (V) is performed at a temperature in the region of 20° C.

The compounds of formula (X) may be prepared by the action of m-chloroperbenzoic acid on a derivative of formula:

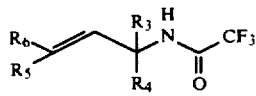

in which $R_3$, $R_4$, $R_5$ and $R_6$ have the same meanings as in the formula (X).

This reaction is preferably performed in a chlorinated solvent such as 1,2-dichloroethane, chloroform or methylene chloride, at a temperature of 0° C.

The derivatives of formula (XI) may be obtained by application or adaptation of the method described by P. HODGE et al., Synthesis, 941, 1984.

According to the invention, the compounds of formula (I) may also be prepared by the action of an amine of formula:

in which $R_2$ has the same meanings as in the formula (I), on a compound of formula:

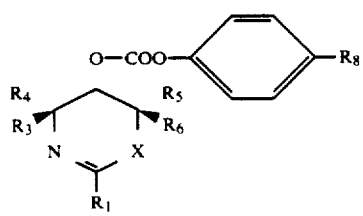

in which $R_8$ denotes a hydrogen atom or a nitro radical and X, $R_1$, $R_3$, $R_4$, $R_5$ and $R_6$ have the same meanings as in the formula (I), or, when one of the substituents $R_3$ or $R_4$ denotes a methyl radical and the other a hydrogen atom, a mixture of these compounds.

This reaction is generally performed in an organic solvent such as acetonitrile, in the presence of a base such as 4-(dimethylamino)pyridine or triethylamine, at a temperature between 50° C. and the boiling point of the solvent.

The compounds of the formula (XIII) may be prepared by the action of phenyl chloroformate or 4-nitrophenyl chloroformate on a compound of formula (III) in which X, $R_1$, $R_3$, $R_4$, $R_5$ and $R_6$ have the same meanings as in the formula (I), or, when one of the substituents $R_3$ or $R_4$ denotes a methyl radical and the other a hydrogen atom, a mixture of these compounds.

This reaction is generally performed in pyridine at a temperature in the region of 20° C.

As those versed in the art may realize, some radicals falling within the definition of the symbol $R_1$ are incompatible with reagents employed during the reactions, and must be protected prior to carrying out the processes or certain phases of the processes described above. This is the case, in particular, when the radical $R_1$ contains primary or secondary amine groups. In this case, the said groups would have to be protected by any method known to those versed in the art, and then be unblocked after the reaction.

The reaction mixtures obtained by the various processes described above may be purified by conventional physical or chemical purification methods (evaporation, extraction, crystallization, chromatography, etc).

The compounds of formula (I), in free base form, may be converted into an addition salt with acids by the action of an acid in an organic solvent such as an alcohol, a ketone, a chlorinated solvent or an ether.

The compounds of formula (I) exhibit advantageous pharmacological properties. These compounds are cholecystokinin (CCK) antagonists, and are hence useful in the treatment and prevention of disorders involving the action of CCK on the nervous system or the gastrointestinal system. Thus, these compounds can be used for the treatment or prevention of psychoses, Parkinson's disease, tardive dyskinesia, irritable colon syndrome, acute pancreatitis, ulcers and disorders of intestinal motility and as an appetite reducer. These compounds also have a potentiating effect on the analgesic activity of narcotic and non-narcotic analgesic drugs.

The anti-CCK activity of the compounds of formula (I) was determined according to a technique based on that of A. SAITO et al., J. Neuro. Chem., 37. 483–490, 1981. In this test, the $IC_50$ of the compounds of formula (I) is less than 1000 nM.

The compounds of formula (I) exhibit low toxicity. Their $LD_50$ is generally more than 40 mg/kg when administered subcutaneously to mice.

Of special importance are the compounds of formula (I) for which:

$R_1$ denotes 2-thienyl, naphthyl, phenyl, or phenyl substituted by one or two halogen atoms, by alkoxy, alkyl, nitro, acyl, alkylthio, trifluoromethoxy, morpholino, piperidino, amino, monoalkylamino or dialkylamino or, at the 3- and 4-positions, by methylenedioxy, $R_2$ denotes phenyl or phenyl substituted by one or two halogen atoms, by alkoxy, nitro, alkyl, hydroxy or trifluoromethyl or, at the 3- and 4-positions, by methylenedioxy, and X denotes oxygen.

The following compounds are especially advantageous:

(4RS, 5RS)-2-(4-chlorophenyl)-4-phenyl-5-phenylcarbamoyloxy-5,6-dihydro-4H-1,3-oxazine (4RS, 5RS)-2-(3,4-methylenedioxyphenyl)-4-phenyl-5-phenylcarbamoyloxy-5,6-dihydro-4H-1,3-oxazine (4RS, 5RS)-2-(4-methoxyphenyl)-4-phenyl-5-phenylcarbamoyloxy-5,6-dihydro-4H-1,3-oxazine (5RS, 6SR)-2,6-diphenyl-5-phenylcarbamoyloxy-5,6-dihydro-4H-1,3-oxazine (5RS, 6SR)-5-(3-chlorophenylcarbamoyloxy)2,6-diphenyl-5,6-dihydro-4H-1,3-oxazine (5RS, 6SR)-5-(3-methylphenylcarbamoyloxy)-2,6-diphenyl-5,6-dihydro-4H-1,3-oxazine (5RS, 6SR)-2-[4-(dimethylamino)phenyl]-6-phenyl-5-phenylcarbamoyloxy-5,6-dihydro-4H-1,3-oxazine (5RS, 6SR)-2-[4-(methylamino)phenyl]-6-phenyl-5-phenylcarbamoyloxy-5,6-dihydro-4H-1,3-oxazine (5RS, 6SR)-2-[4-(ethylthio)phenyl]-6-phenyl-5-phenylcarbamoyloxy-5,6-dihydro-4H-1,3-oxazine (5RS, 6SR)-5-(3-hydroxyphenylcarbamoyloxy)-2,6-diphenyl-5,6-dihydro-4H-1,3-oxazine (5RS, 6SR)-2-(4-methoxyphenyl)-6-phenyl-5-phenylcarbamoyloxy-5,6-dihydro-4H-1,3-oxazine (5RS, 6SR)-2-(4-chlorophenyl)-6-phenyl-5-phenylcarbamoyloxy-5,6-dihydro-4H-1,3-oxazine 5RS, 6SR)-2-(2-fluorophenyl)-6-phenyl-5-phenylcarbamoyloxy-5,6-dihydro-4H-1,3-oxazine (5RS, 6SR)-2-(3,4-dichlorophenyl)-6-phenyl-5-phenylcarbamoyloxy-5,6-dihydro-4H-1,3-oxazine phenylcarbamoyloxy-5,6-dihydro-4H-1,3-oxazine (5RS, 6SR)-2-(4-fluorophenyl)-6-phenyl-5-phenylcarbamoyloxy-5,6-dihydro-4H-1,3-oxazine (4RS, 5RS)-5-(3,4-dichlorophenylcarbamoyloxy)-2,4-diphenyl-5,6-dihydro-4H-1,3-oxazine (5RS, 6SR)-6-phenyl-5-phenylcarbamoyloxy-2-(2-thienyl)-5,6-dihydro-4H-1,3-oxazine (4RS, 5RS)-5-(3,4-methylenedioxyphenylcarbamoyloxy)-2,4-diphenyl-5,6-dihydro-4H-1,3-oxazine (5RS, 6SR)-5-(3-methoxyphenylcarbamoyloxy)-2,6-diphenyl-5,6-dihydro-4H-1,3-oxazine (5RS, 6SR)-5-(3-nitrophenylcarbamoyloxy)-2,6-diphenyl-5,6-dihydro-4H-1,3-oxazine (5RS, 6SR)-6-methyl-2,6-diphenyl-5-phenylcarbamoyloxy-5,6-dihydro-4H-1,3-oxazine (5RS, 6SR)-2-(4-acetylphenyl)-6-phenyl-5-phenylcarbamoyloxy-5,6-dihydro-4H-1,3-oxazine (5RS, 6SR)-2-(4-isopropylphenyl)-6-phenyl-5-phenylcarbamoyloxy-5,6-dihydro-4H-1,3-oxazine (5RS, 6SR)-2-(4-morpholinophenyl)-6-phenyl-5-phenylcarbamoyloxy-5,6-dihydro-4H-1,3-oxazine (5RS, 6SR)-2-(4-piperidinophenyl)-6-phenyl-5-phenylcarbamoyloxy-5,6-dihydro-4H-1,3-oxazine.

For therapeutic use, the compounds of formula (I) may be used as the free bases or as pharmaceutically acceptable acid adition salts. As examples of salts, there may be mentioned the addition salts with inorganic acids, such as hydrochorides, sulphates, nitrates and phosphates, and organic acids, such as acetates, propionates, succinates, benzoates, fumarates, maleates, methanesulphonates, isethionates, theophyllineacetates, salicylates, phenolphthalinates and methylene-bis(β-hydroxynaphthoates), or substitution derivatives of these derivatives.

The Examples which follow illustrate the invention:

EXAMPLE 1

Phenyl isocyanate (9 g) is added at a temperature in the region of 20° C. to a solution, maintained under an argon atmosphere, of (4RS, 5RS)-2,4-diphenyl-5,6-dihydro-4H-1,3-oxazin-5-ol (18 g) in 1,2-dichloroethane (200 cc). The solution obtained is stirred under reflux for 2 hours and then concentrated to dryness under reduced pressure (2.7 kPa). The residue is purified by chromatography on silica (0.063–0.2 mm; 400 g) contained in a column 7 cm in diameter, collecting 50-cc fractions. Fractions 1 to 12, eluted with a mixture of ethyl acetate and cyclohexane (1:6 by volume), are combined and concentrated to dryness under reduced pressure (2.7 kPa) at 40° C. After recrystallization from acetonitrile, (4RS, 5RS)-2,4-diphenyl-5-phenylcarbamoyloxy-5,6-dihydro-4H-1,3-oxazine (7 g) m.p. 163° C., is obtained.

(4RS, 5RS)-2,4-Diphenyl-5,6-dihydro-4H-1,3-oxazin-5-ol may be prepared in the following manner: tosyl chloride (4.2 g) is added at a temperature in the region of 20° C. to a solution, maintained under an argon atmosphere, of N-[(1RS, 2RS)-2,3-dihydroxy-1-phenylpropyl]benzamide (5.42 g) and triethylamine (8.35 cc) in 1,2-dichloroethane (200 cc). The solution obtained is stirred at a temperature in the region of 70° C. for 4 hours and then added to distilled water (200 cc). The organic phase is washed with distilled water (2 × 100 cc) and then with brine (100 cc), dried over magnesium sulphate, filtered and then concentrated to dryness under reduced pressure (2.7 kPa) at 40° C. After recrystallization in acetonitrile, (4RS, 5RS)-2,4-diphenyl-5,6-dihydro-4H-1,3-oxazin-5-ol (2.6 g), m.p. 150° C., is obtained.

N-[(1RS, 2RS)-2,3-Dihydroxy-1-phenylpropyl]benzamide may be prepared according to the method described by T. SUAMI, I. UCHIDA, S. UMEZAWA, Bull. Chem. Soc. Japan, 1956, 29, 417.

EXAMPLE 2

3,4-Dichlorophenyl isocyanate (1.15 g) is added at a temperature in the region of 20° C. to a solution, maintained under an argon atmosphere, of (4RS, 5RS)-2,4-diphenyl-5,6-dihydro-4H-1,3-oxazin-5-ol (1.52 g) in 1,2-dichloroethane (20 cc). The solution obtained is heated to reflux for 6 hours and then concentrated to dryness under reduced pressure (2.7 kPa). After recrystallization in acetonitrile, (4RS, 5RS)-5-(3,4-dichlorophenylcarbamoyloxy)-2,4-diphenyl-5,6-dihydro-4H-1,3-oxazine (2 g), m.p. 184° C., is obtained.

EXAMPLE 3

4-Methoxyphenyl isocyanate (1 g) is added at a temperature in the region of 20° C. to a solution, maintained under an argon atmosphere, of (4RS, 5RS)-2,4-diphenyl-5,6-dihydro-4H-1,3-oxazin-5-ol (1.7 g) in 1,2-dichloroethane (20 cc). The solution obtained is stirred under reflux for 4 hours and then concentrated to dryness under reduced pressure (2.7 kPa). The residue is purified by chromatography on silica (0.063–0.2 mm; 40 g) contained in a column 2 cm in diameter, collecting 20-cc fractions. Fractions 2 to 6, eluted with a mixture of ethyl acetate and cyclohexane (3:7 by volume), are combined and concentrated to dryness under reduced pressure (2.7 kPa) at 40° C. After recrystallization in diisopropyl ether, (4RS, 5RS)-5-(4-methoxyphenylcarbamoyloxy)-2,4-diphenyl-5,6-dihydro-4H-1,3-oxazine (0.7 g), m.p. 140° C., is obtained.

EXAMPLE 4

4-Nitrophenyl isocyanate (1.08 g) is added at a temperature in the region of 20° C. to a solution, maintained under an argon atmosphere, of (4RS, 5RS)-2,4-diphenyl-5,6-dihydro-4H-1,3-oxazin-5-ol (1.5 g) in 1,2-dichloroethane (20 cc). The solution obtained is heated to reflux for 4 hours and then concentrated to dryness under reduced pressure (2.7 kPa). The residue is purified by chromatography on silica (0.063–0.2 mm; 40 g) contained in a column 2 cm in diameter, collecting 20-cc fractions. Fractions 2 to 7, eluted with a mixture of ethyl acetate and cyclohexane (2:3 by volume), are combined and concentrated to dryness under reduced pressure (2.7 kPa) at 40° C. After recrystallization in a mixture of ethyl acetate and diisopropyl ether (1:1 by volume), (4RS, 5RS)-5-(4-nitrophenylcarbamoyloxy)-2,4-diphenyl-5,6-dihydro-4H-1,3-oxazine (0.8 g), m.p. 220° C., is obtained.

EXAMPLE 5

3- Chlorophenyl isocyanate (0.8 g) is added at a temperature in the region of 20° C. to a solution, maintained under an argon atmosphere, of (4RS, 5RS)-2,4-diphenyl-5,6-dihydro-4H-1,3-oxazin-5-ol (1.2 g) in 1,2-dichloroethane (20 cc). The solution obtained is heated to reflux for 7 hours 30 minutes and then concentrated to dryness under reduced pressure (2.7 kPa). The residue is purified by chromatography on silica (0.063–0.2 mm; 40 g) contained in a column 2 cm in diameter, collecting 15-cc fractions. Fractions 1 to 3, eluted with a mixture of ethyl acetate and cyclohexane (3:7 by volume) are combined and concentrated to dryness under reduced pressure (2.7 kPa) at 40° C. After recrystallization in acetonitrile, (4RS, 5RS)-5-(3-chlorophenylcarbamoyloxy)-2,4-diphenyl-5,6-dihydro-4H-1,3-oxazine (1.4 g), m.p. 160° C., is obtained.

EXAMPLE 6

4-Chlorophenyl isocyanate (1 g) is added at a temperature in the region of 20° C. to a solution, maintained under an argon atmosphere, of (4RS, 5RS)-2,4-diphenyl-5,6-dihydro-4H-1,3-oxazin-5-ol (1.2 g) in 1,2-dichloroethane (20 cc). The solution obtained is heated to reflux for 7 hours 30 minutes and then concentrated to dryness under reduced pressure (2.7 kPa). After two successive recrystallizations in acetonitrile, (4RS, 5RS)-5-(4-chlorophenylcarbamoyloxy)-2,4-diphenyl-5,6-dihydro-4H-1,3-oxazine (1.1 g), m.p. 200° C., is obtained.

EXAMPLE 7

4-(Trifluoromethyl)phenyl isocyanate (0.8 g) is added at a temperature in the region of 20° C. to a solution, maintained under an argon atmosphere, of (4RS, 5RS)-2,4-diphenyl-5,6-dihydro-4H-1,3-oxazin-5-ol (1.26 g) in 1,2-dichloroethane (30 cc). The solution obtained is heated to reflux for 5 hours and then concentrated to dryness under reduced pressure (2.7 kPa). The residue is purified by chromatography on silica (0.063–0.2 mm; 40 g) contained in a column 1 cm in diameter, collecting 20-cc fractions. Fractions 2 and 3, eluted with a mixture of ethyl acetate and cyclohexane (3:7 by volume), are combined and concentrated to dryness under reduced pressure (2.7 kPa) at 40° C. After recrystallization in petroleum ether, (4RS, 5RS)-2,4-diphenyl-5-[4-(trifluoromethyl)phenylcarbamoyloxy]-5,6-dihydro-4H-1,3-oxazine (1.4 g), m.p. 140° C., is obtained.

EXAMPLE 8

Phenyl isocyanate (2.3 g) is added at a temperature in the region of 20° C. to a solution, maintained under an argon atmosphere, of (4RS, 5RS)-2-(2-indolyl)-4-phenyl-5,6-dihydro-4H-1,3-oxazin-5-ol (5.15 g) in 1,2-dichloroethane (50 cc). The solution obtained is stirred for 7 hours under reflux and then concentrated to dryness under reduced pressure (2.7 kPa) at 40° C. After two successive recrystallizations in diisopropyl ether, (4RS, 5RS)-2-(2-indolyl)-4-phenyl-5-phenylcarbamoyloxy-5,6-dihydro-4H-1,3-oxazine (4 g), m.p. 166° C., is obtained.

(4RS, 5RS)-2-(2-Indolyl)-4-phenyl-5,6-dihydro-4H-1,3-oxazin-5-ol may be prepared in the following manner: tosyl chloride (13.77 g) is added at a temperature in the region of 20° C. to a solution, maintained under an argon atmosphere, of N-[(1RS, 2RS)-2,3-dihydroxy-1-phenylpropyl]-2-indolecarboxamide (18.6 g) in pyridine (200 cc). The solution obtained is stirred for 6 hours at a temperature in the region of 40° C. and then for 16 hours at a temperature in the region of 20° C., and is thereafter poured into water (1800 cc). The mixture is extracted with ethyl acetate (3 × 250 cc) and the organic phases are combined, washed with water, dried over magnesium sulphate, filtered and concentrated to dryness under reduced pressure (2.7 kPa) at 40° C. The residue is purified by chromatography on silica (0.063–0.2 mm; 500 g) contained in a column 7 cm in diameter, collecting 50-cc fractions. Fractions 3 to 10, eluted with a mixture of ethyl acetate and cyclohexane (1:1 by volume), are combined and concentrated to dryness under reduced pressure (2.7 kPa) at 40° C. After recrystallization in ethyl acetate, (4RS, 5RS)-2-(2-indolyl)-4-phenyl-5,6-dihydro-4H-1,3-oxazin-5-ol (3.2 g), m.p. 204° C., is obtained.

N-[(1RS, 2RS)-2,3-Dihydroxy-1-phenylpropyl]-2-indolecarboxamide may be prepared in the following manner: oxalyl dichloride (5.15 cc), dissolved in diethyl ether (10 cc), is added dropwise at a temperature in the region of 20° C. to a solution, maintained under an argon atmosphere, of 2-indolecarboxylic acid (8.05 g) and dimethylformamide (0.1 cc) in diethyl ether (90 cc). The solution obtained is stirred for 3 hours at a temperature in the region of 20° C. and then added dropwise to a solution, maintained under an argon atmosphere of (2RS, 3RS)-3-amino-3-phenyl-1,2-propanediol (7.6 g) and triethylamine (8.45 cc) in dichloromethane (100 cc). The suspension is stirred for 2 hours at a temperature in the region of 20° C. and then poured into distilled water (200 cc). The precipitate is filtered off, washed with distilled water and dried. After two successive recrystallizations in ethyl acetate, N-[(1RS, 2RS)-2,3-dihydroxy-1-phenylpropyl]-2-indolecarboxamide (5.8 g), m.p. 151° C., is obtained.

(2RS, 3RS)-3-Amino-3-phenyl-1,2-propanediol may be prepared according to the method described by M. F. SAETONE, Il farmaco-Ed. Sc., 1966, 31(3), 209.

EXAMPLE 9

Phenyl isocyanate (0.5 g) is added at a temperature in the region of 20° C. to a solution, maintained under an argon atmosphere, of (4RS, 5RS)-2-(4-chlorophenyl)-4-phenyl-5,6-dihydro-4H-1,3-oxazin-5-ol (1.1 g) in 1,2-dichloroethane (20 cc). The solution obtained is heated to 70° C. for 2 hours and then concentrated to dryness under reduced pressure (2.7 kPa). The residue is purified by chromatography on silica (0.063–0.2 mm; 40 g) contained in a column 2 cm in diameter, collecting 20-cc fractions. Fractions 2 to 5, eluted with a mixture of dichloromethane and methanol (98:2 by volume), are combined and concentrated to dryness under reduced pressure (2.7 kPa) at 40° C. After recrystallization in a mixture of diisopropyl ether and ethyl acetate (1:1 by volume), (4RS, 5RS)-2-(4-chlorophenyl)-4-phenyl-5-phenylcarbamoyloxy-5,6-dihydro-4H-1,3-oxazine (1.25 g), m.p. 171° C., is obtained.

(4RS, 5RS)-2-(4-Chlorophenyl)-4-phenyl-5,6-dihydro-4H-1,3-oxazin-5-ol may be prepared in the following manner: tosyl chloride (2.9 g) is added at a temperature in the region of 60° C. to a solution, maintained under an argon atmosphere, of N-[(1RS, 2RS)-2,3-dihydroxy-1-phenylpropyl]-4-chlorobenzamide (3.2 g) and triethylamine (4.4 cc) in 1,2-dichloroethane (80 cc). The solution obtained is heated for 16 hours to a temperature in the region of 60° C. and then added to distilled water (50 cc). The aqueous phase is neutralized with 5 N aqueous hydrochloric acid solution and then extracted with dichloromethane (3×50 cc). The organic phases are combined, washed with water, dried over magnesium sulphate, filtered and concentrated to dryness under reduced pressure (2.7 kPa) at 40° C. The residue is purified by chromatography on silica (0.063–0.2 mm; 100 g) contained in a column 3 cm in diameter, collecting 25-cc fractions. Fractions 3 to 10, eluted with a mixture of ethyl acetate and cyclohexane (2:3 by volume), are combined and concentrated to dryness under reduced pressure (2.7 kPa) at 40° C. After recrystallization in diisopropyl ether, (4RS, 5RS)-2-(4-chlorophenyl)-4-phenyl-5,6-dihydro-4H-1,3-oxazin-5-ol (1.1 g), m.p. 142° C., is obtained.

N-[(1RS, 2RS)-2,3-Dihydroxy-1-phenylpropyl]-4-chlorobenzamide may be prepared in the following manner: working as in Example 8 for the preparation of N-[(1RS, 2RS)-2,3-dihydroxy-1-phenylpropyl]-2-indolecarboxamide, but starting with 4-chlorobenzoic acid (2.57 g), oxalyl dichloride (1.55 cc), (2RS, 3RS)-3-amino-3-phenyl-1,2-propanediol (2.5 g) and triethylamine (8.3 cc), and after the precipitate is washed with distilled water and then with diisopropyl ether, N-[(1RS, 2RS)-2,3-dihydroxy-1-phenylpropyl]-4-chlorobenzamide (3.2 g), m.p. 142° C., is obtained.

EXAMPLE 10

Phenyl isocyanate (0.84 g) is added at a temperature in the region of 20° C. to a solution, maintained under an argon atmosphere, of (4RS, 5RS)-2-(3,4-methylenedioxyphenyl)-4-phenyl-5,6-dihydro-4H-1,3-oxazin-5-ol (1.9 g) in 1,2-dichloroethane (30 cc). The solution obtained is heated to 80° C. for 4 hours and then concentrated to dryness under reduced pressure (2.7 kPa). The residue is purified by chromatography on silica (0.063–0.2 mm; 100 g) contained in a column 3 cm in diameter, collecting 20-cc fractions. Fractions 2 to 8, eluted with a mixture of dichloromethane and methanol (98:2 by volume), are combined and concentrated to dryness under reduced pressure (2.7 kPa) at 40° C. After recrystallization in a mixture of diisopropyl ether and ethyl acetate (1:1 by volume), (4RS, 5RS)-2-(3,4-methylenedioxyphenyl)-4-phenyl-5-phenylcarbamoyloxy-5,6-dihydro-4H-1,3-oxazine (1.3 g), m.p. 115° C., is obtained.

(4RS, 5RS)-2-(3,4-Methylenedioxyphenyl)-4-phenyl-5,6-dihydro-4H -1,3-oxazin-5-ol may be prepared in the following manner: tosyl chloride (4 g) is added at a temperature in the region of 60° C. to a solution, maintained under an argon atmosphere, of N-[(1RS, 2RS)-2,3-dihydroxy-1-phenylpropyl]-3,4-methylenedioxybenzamide (6 g) and triethylamine (8 cc) in 1,2-dichloroethane (80 cc). The solution obtained is heated for 16 hours at a temperature in the region of 60° C. and then added to distilled water (50 cc). The aqueous phase is neutralized with 5 N aqueous hydrochloric acid solution and then extracted with dichloromethane (3×50 cc). The organic phases are combined, washed with water, dried over magnesium sulphate, filtered and concentrated to dryness under reduced pressure (2.7 kPa) at 40° C. The residue is purified by chromatography on silica (0.063–0.2 mm; 200 g) contained in a column 3 cm in diameter, collecting 25-cc fractions. Fraction 5 to 10, eluted with a mixture of ethyl acetate and cyclohexane (1:1 by volume), are combined and concentrated to dryness under reduced pressure (2.7 kPa) at 40° C. After recrystallization in diisopropyl ether, (4RS, 5RS)-2-(3,4-methylenedioxyphenyl)-4-phenyl-5,6-dihydro-4H-1,3-oxazin-5-ol (1.9 g), m.p. 137° C., is obtained.

N-[(1RS, 2RS)-2,3-Dihydroxy-1-phenylpropyl]-3,4-methylenedioxybenzamide may be prepared in the following manner: working as in Example 8 for the preparation of N-[(1RS, 2RS)-2,3-dihydroxy-1-phenylpropyl]-2-indolecarboxamide but starting with piperonylic acid (4.6 g), oxalyl dichloride (2.6 cc), (2RS, 3RS)-3-amino-3-phenyl-1,2-propanediol (4.17 g) and triethylamine (10.5 cc), and after the precipitate is washed with distilled water and then with diisopropyl ether, N-[(1RS, 2RS)-2,3-dihydroxy-1-phenylpropyl]-3,4-methylenedioxybenzamide (6 g), m.p. 172° C., is obtained.

EXAMPLE 11

Phenyl isocyanate (0.6 g) is added at a temperature in the region of 20° C. to a solution, maintained under an argon atmosphere, of (4RS, 5RS)-2-(4-methoxyphenyl)-4-phenyl-5,6-dihydro-4H-1,3-oxazin-5-ol (1.75 g) in 1,2-dichloroethane (20 cc). The solution obtained is heated to 60° C. for 4 hours and then concentrated to dryness under reduced pressure (2.7 kPa). The residue is purified by chromatography on silica (0.063–0.2 mm; 100 g) contained in a column 3 cm in diameter, collecting 20-cc fractions. Fractions 2 to 6, eluted with a mixture of ethyl acetate and cyclohexane (3:7 by volume) are combined and concentrated to dryness under reduced pressure (2.7 kPa) at 40° C. After recrystallization in a mixture of diisopropyl ether and ethyl acetate (1:1 by volume), (4RS, 5RS)-2-(4-methoxyphenyl)-4-phenyl-5-phenylcarbamoyloxy-5,6-dihydro-4H-1,3-oxazine (1.2 g), m.p. 105° C., is obtained.

(4RS, 5RS)-2-(4-Methoxyphenyl)-4-phenyl-5,6-dihydro-4H-1,3-oxazin-5-ol may be prepared in the following manner: tosyl chloride (3.82 g) is added at a temperature in the region of 60° C. to a solution, maintained under an argon atmosphere, of N-[(1RS, 2RS)2,3-dihydroxy-1-phenylpropyl]-4-methoxybenzamide (5.5 g) and triethylamine (7.7 cc) in 1,2-dichloroethane (80 cc). The solution obtained is heated for 16 hours to a temperature in the region of 60° C. and then added to distilled water (50 cc). The aqueous phase is neutralized with 5 N aqueous hydrochloric acid solution and then extracted with dichloromethane (3×50 cc). The organic phases are combined, washed with water, dried over magnesium sulphate, filtered and concentrated to dryness under reduced pressure (2.7 kPa) at 40° C. The residue is purified by chromatography on silica (0.063–0.2 mm; 200 g) contained in a column 3 cm in diameter, collecting 25-cc fractions. Fractions 3 to 9, eluted with a mixture of ethyl acetate and cyclohexane (1:1 by volume), are combined and concentrated to dryness under reduced pressure (2.7 kPa) at 40° C. After recrystallization in ethyl acetate (4RS, 5RS)-2-(4-methoxyphenyl)-4-phenyl-5,6-dihydro-4H-1,3-oxazin-5-ol (1.41 g), m.p. 144° C., is obtained.

N-[(1RS, 2RS)-2,3-Dihydroxy-1-phenylpropyl]-4-methoxybenzamide may be prepared in the following manner: working as in Example 8 for the preparation of N-[(1RS, 2RS)-2,3-dihydroxy-1-phenylpropyl]-2-indolecarboxamide, but starting with 4-methoxybenzoic acid (3.7 g), oxalyl dichloride (2.26 cc), (2RS, 3RS)-3-amino-3-phenyl-1,2-propanediol (3.7 g) and triethylamine (9.26 cc) and after the precipitate is washed with distilled water and then with diisopropyl ether, N-[(1RS, 2RS)-2,3dihydroxy-1-phenylpropyl]-4-methoxybenzamide (5.5 g), m.p. 178° C., is obtained.

EXAMPLE 12

Phenyl isocyanate (0.33 g) is added at a temperature in the region of 20° C. to a solution, maintained under an argon atmosphere of (5RS, 6SR)-2,6-diphenyl-5,6-dihydro-4H-1,3-oxazin-5-ol (0.4 g) in 1,2-dichloroethane (10 cc). The solution obtained is stirred under reflux for 4 hours and then concentrated to dryness under reduced pressure (2.7 kPa). The residue is purified by chromatography on silica (0.063–0.2 mm; 50 g) contained in a column 2 cm in diameter, collecting 20-cc fractions. Fractions 5 to 11, eluted with a mixture of ethyl acetate and cyclohexane (3:7 by volume), are combined and concentrated to dryness under reduced pressure (2.7 kPa) at 40° C. After recrystallization in petroleum ether, (5RS, 6SR)-2,6-diphenyl-5-phenylcarbamoyloxy-5,6-dihydro-4H-1,3-oxazine (0.36 g), m.p. 111° C., is obtained.

(5RS, 6SR)-2,6-Diphenyl-5,6-dihydro-4H-1,3-oxazin-5-ol may be prepared in the following manner. A 0.55 M solution (272 cc) of 3-chloroperbenzoic acid in dichloromethane is added dropwise at a temperature in the region of 0° C. to a solution, maintained under an argon atmosphere, of (E)-N-cinnamylbenzamide (35.5 g) in dichloromethane (150 cc). The suspension obtained is stirred at a temperature in the region of 0° C. for 2 hours and then filtered. To the filtrate maintained under an argon atmosphere, boron trifluoride etherate (21 cc) is added dropwise at a temperature in the region of 0° C. The mixture is then stirred for 1 hour at a temperature in the region of 20° C. and thereafter poured into distilled water (150 cc). The organic phase is washed successively with 1 N aqueous sodium thiosulphate solution (100 cc), distilled water (50 cc) and 1 N aqueous sodium hydroxide solution (150 cc), filtered on celite, dried over magnesium sulphate, filtered and then concentrated to dryness under reduced pressure (2.7 kPa) at 40° C. After recrystallization in ethyl acetate, (5RS, 6SR)-2,6-diphenyl-5,6-dihydro-4H-1,3-oxazin-5-ol (18 g), m.p. 135° C., is obtained.

(E)-N-Cinnamylbenzamide may be prepared according to the method described by A. PADWA, J. T. BLACKLOCK, Per H. J. CARLSEN and M. PULWER, J. Org. Chem., 44(19), 3281, 1979.

EXAMPLE 13

A solution of (5RS, 6SR)-2,6-diphenyl-5,6-dihydro-4H-1,3-oxazin-5-ol (1.52 g) in anhydrous tetrahydrofuran (10 cc) is added at a temperature in the region of 20° C. to an oily suspension (50% by weight; 0.31 g), maintained under an argon atmosphere, of sodium hydride in anhydrous tetrahydrofuran (20 cc). The mixture is stirred for 30 minutes at the same temperature. A solution of 4-chlorophenyl isocyanate (1 g) in anhydrous tetrahydrofuran (10 cc) is then added dropwise and stirring is continued for 3 hours at a temperature in the region of 20° C. Distilled water (25 cc) is then added and the mixture is extracted with dichloromethane (3×50 cc). The organic phases are combined, washed with distilled water (3×20 cc), dried over magnesium sulphate and concentrated to dryness under reduced pressure (2.7 kPa) at 40° C. The residue is purified by chromatography on silica (0.063–0.2 mm; 50 g) contained in a column 2 cm in diameter [eluent: ethyl acetate/cyclohexane (2:3 by volume)], collecting 20-cc fractions. Fractions 4 to 6 are combined and concentrated to dryness under reduced pressure (2.7 kPa) at 40° C. After recrystallization in diisopropyl ether, (5RS, 6SR)-5-(4-chlorophenylcarbamoyloxy)-2,6-diphenyl-5,6-dihydro-4H-1,3-oxazine (1 g), m.p. 124° C. is obtained.

EXAMPLE 14

A solution of (5RS, 6SR)-2,6-diphenyl-5,6-dihydro-4H-1,3-oxazin-5-ol (1.52 g) in anhydrous tetrahydrofuran (10 cc) is added at a temperature in the region of 20° C. to an oily suspension (50% by weight; 0.31 g), maintained under an argon atmosphere, of sodium hydride in anhydrous tetrahydrofuran (20 cc). The mixture is stirred for 30 minutes at the same temperature. A solution of 3-chlorophenyl isocyanate (1 g) in anhydrous tetrahydrofuran (10 cc) is then added dropwise and stirring is continued for 3 hours at a temperature in the region of 20° C. Distilled water (25 cc) is then added and the mixture is extracted with dichloromethane (3×50 cc). The organic phases are combined, washed with distilled water (3×20 cc), dried over magnesium sulphate and concentrated to dryness under reduced pressure (2.7 kPa) at 40° C. After recrystallization in a mixture of ethyl acetate and diisopropyl ether (1:1 by volume), (5RS, 6SR)-5-(3-chlorophenylcarbamoyloxy)-2,6-diphenyl-5,6-dihydro-4H-1,3-oxazine (0.56 g), m.p. 160° C. is obtained.

EXAMPLE 15

A solution of (5RS, 6SR)-2,6-diphenyl-5,6-dihydro-4H-1,3-oxazin-5-ol (1.52 g) in anhydrous tetrahydrofuran (10 cc) is added at a temperature in the region of 20° C. to an oily suspension (50% by weight; 0.31 g), maintained under an argon atmosphere, of sodium hydride in anhydrous tetrahydrofuran (20 cc), and the solution obtained is stirred for 30 minutes at the same temperature. A solution of 3,4-dichlorophenyl isocyanate (1.24 g) in anhydrous tetrahydrofuran (10 cc) is then added dropwise and stirring is continued for 3 hours at a temperature in the region of 20° C. Distilled water (25 cc) is then added and the mixture is extracted with dichloromethane (3×50 cc). The organic phases are combined, washed with distilled water (3×20 cc), dried over magnesium sulphate and concentrated to dryness under reduced pressure (2.7 kPa) at 40° C. The residue is purified by chromatography on silica (0.063–0.2 mm; 50 g) contained in a column 2 cm in diameter [eluent: ethyl acetate/cyclohexane (3:7 by volume)], collecting 20-cc fractions. Fractions 6 to 9 are combined and concentrated to dryness under reduced pressure (2.7 kPa) at 40° C. (5RS, 6SR)-5-(3,4-Dichlorophenylcarbamoyloxy)-2,6-diphenyl-5,6-dihydro-4H-1,3-oxazine (1.1 g), m.p. 80° C., is thereby obtained.

EXAMPLE 16

A solution of (5RS, 6SR)-2,6-diphenyl-5,6-dihydro-4H-1,3-oxazin-5-ol (1.52 g) in anhydrous tetrahydrofuran (10 cc) is added at a temperature in the region of 20° C. to an oily suspension (50% by weight; 0.31 g), maintained under an argon atmosphere, of sodium hydride in anhydrous tetrahydrofuran (20 cc). The mixture is stirred for 30 minutes at the same temperature. A solution of 4-fluorophenyl isocyanate (0.9 g) in anhydrous tetrahydrofuran (10 cc) is then added dropwise and stirring is continued for 4 hours at a temperature in the region of 20° C. Distilled water (25 cc) is then added and the mixture is extracted with dichloromethane (3×50 cc). The organic phases are combined, washed with distilled water (3×20 cc), dried over magnesium sulphate and concentrated to dryness under reduced pressure (2.7 kPa) at 40° C. The residue is purified by chromatography on silica (0.063–0.2 mm; 50 g) contained in a column 2 cm in diameter [eluent: ethyl acetate/cyclohexane (3:7 by volume)], collecting 20-cc fractions. Fractions 3 to 5 are combined and concentrated to dryness under reduced pressure (2.7 kPa) at 40° C. After recrystallization in diisopropyl ether, (5RS, 6SR)-5-(4-fluorophenylcarbamoyloxy)-2,6-diphenyl-5,6-dihydro-4H-1,3-oxazine (0.8 g), m.p. 158° C., is obtained.

EXAMPLE 17

Working in a manner similar to that described in Example 16, but starting with an oily suspension (50% by weight; 0.31 g) of sodium hydride, (5RS, 6SR)-2,6-diphenyl-5,6-dihydro-4H-1,3-oxazin-5-ol (1.52 g) and 2-fluorophenyl isocyanate (0.9 g), and after recrystallization in diisopropyl ether, (5RS, 6SR)-5-(2-fluorophenylcarbamoyloxy)-2,6-diphenyl-5,6-dihydro-4H-1,3-oxazine (0.67 g), m.p. 98° C., is obtained.

EXAMPLE 18

3-Methylphenyl isocyanate (1 g) is added at a temperature in the region of 20° C. to a solution, maintained under an argon atmosphere, of (5RS, 6SR)-2,6-diphenyl-5,6-dihydro-4H-1,3-oxazin-5-ol (1.77 g) and 4-(dimethylamino)pyridine (0.15 g) in 1,2-dichloroethane (30 cc). The solution obtained is heated to reflux for 4 hours and then concentrated to dryness under reduced pressure (2.7 kPa). The residue is purified by chromatography on silica (0.063–0.2 mm; 50 g) contained in a column 2 cm in diameter [eluent: ethyl acetate/cyclohexane (3:7 by volume)], collecting 20-cc fractions. Fractions 5 to 7 are combined and concentrated to dryness under reduced pressure (2.7 kPa) at 40° C. (5RS, 6SR)-5-(3-Methylphenylcarbamoyloxy)-2,6-diphenyl-5,6-dihydro-4H-1,3-oxazine (1 g), m.p 80° C., is thereby obtained.

EXAMPLE 19

Phenyl isocyanate (1.25 g) is added at a temperature in the region of 20° C. to a solution, maintained under an argon atmosphere, of (5RS, 6SR)-2-(4-methoxyphenyl)-6-phenyl-5,6-dihydro-4H-1,3-oxazin-5-ol (1.5 g) in 1,2-dichloroethane (20 cc). The solution obtained is heated to reflux for 6 hours and then concentrated to dryness under reduced pressure (2.7 kPa). The residue is purified by chromatography on silica (0.063–0.2 mm; 50 g) contained in a column 2 cm in diameter [eluent: cyclohexane/ethyl acetate/triethylamine (60:35:5 by volume)], collecting 20-cc fractions. Fractions 4 to 10 are combined and concentrated to dryness under reduced pressure (2. 7 kPa) at 40° C. After recrystallization in diisopropyl ether, (5RS, 6SR)-2-(4-methoxyphenyl)-6-phenyl-5-phenylcarbamoyloxy-5,6-dihydro-4H-1,3-oxazine (0.52 g), m.p. 223° C., is obtained.

(5RS, 6SR)-2-(4-Methoxyphenyl)-6-phenyl-5,6-dihydro-4H-1,3-oxazin-5-ol may be prepared in the following manner: a 0.54 M solution (37 cc) of 3-chloroperbenzoic acid in dichloromethane is added dropwise at a temperature in the region of 0° C. to a solution, maintained under an argon atmosphere, of (E)-N-cinnamyl-4-methoxybenzamide (4.77 g) in dichloromethane (30 cc). The suspension obtained is stirred at a temperature in the region of 0° C. for 1 hour 30 minutes and then filtered. To the filtrate, maintained under an argon atmosphere, boron trifluoride etherate (2.4 cc) is added dropwise at a temperature in the region of 0° C. The mixture is then stirred for 1 hour at a temperature in the region of 20° C. and thereafter hydrolyzed with 1 N aqueous sodium hydroxide solution (19.6 cc). The organic phase is separated and then washed successively with 1 N aqueous sodium thiosulphate solution (30 cc), distilled water (30 cc) and saturated aqueous sodium bicarbonate solution (30 cc), dried over magnesium sulphate, filtered and then concentrated to dryness under reduced pressure (2.7 kPa) at 40° C. After recrystallization in a mixture of ethyl acetate and diisopropyl ether (1:1 by volume), (5RS, 6SR)-2-(4-methoxyphenyl)-6-phenyl-5,6-dihydro-4H-1,3-oxazin-5-ol (2.6 g), m.p. 132° C., is obtained.

(E)-N-Cinnamyl-4-methoxybenzamide may be prepared in the following manner: oxalyl dichloride (2.6 cc), dissolved in diethyl ether (10 cc), is added dropwise at a temperature in the region of 20° C. to a solution, maintained under an argon atmosphere, of 4-methoxybenzoic acid (4.2 g) and dimethylformamide (0.1 cc) in diethyl ether (40 cc). The solution obtained is stirred for 1 hour 30 minutes at a temperature in the region of 20° C. and then added dropwise to a solution, maintained under an argon atmosphere, of (E)-cinnamylamine (3.3 g) and triethylamine (7 cc) in dichloromethane (50 cc). The suspension is stirred for 30 minutes at a temperature in the region of 30° C. and then poured into distilled water (50 cc). The aqueous phase is acidified to a pH in the region of 5 with 5 N aqueous hydrochloric acid solution and extracted with dichloromethane (2×50 cc). The organic phases are combined, washed with distilled water (2×50 cc), dried over magnesium sulphate, filtered and then concentrated to dryness under reduced pressure (2.7 kPa) at 40° C. After recrystallization in a mixture of ethyl acetate and diisopropyl ether (1:1 by volume), (E)-N-cinnamyl-4-methoxybenzamide (4.72 g), m.p. 132° C., is obtained.

EXAMPLE 20

A solution of (5RS, 6SR)-2-(4-chlorophenyl)-6-phenyl-5,6-dihydro-4H-1,3-oxazin-5-ol (1.8 g) in anhydrous tetrahydrofuran (10 cc) is added at a temperature in the region of 20° C. to an oily suspension (50% by weight; 0.33 g), maintained under an argon atmosphere, of sodium hydride in anhydrous tetrahydrofuran (20 cc). The mixture is stirred for 1 hour and 30 minutes at the same temperature. A solution of phenyl isocyanate (0.9 g) in anhydrous tetrahydrofuran (10 cc) is then added dropwise and stirring is continued for 30 minutes at a temperature in the region of 20° C. Distilled water (25 cc) is then added and the mixture is extracted with dichloromethane (3×50 cc). The organic phases are combined, washed with distilled water (3×20 cc), dried over magnesium sulphate and concentrated to dryness under reduced pressure (2.7 kPa) at 40° C. The residue is purified by chromatography on silica (0.063–0.2 mm; 50 g) contained in a column 2 cm in diameter [eluent: ethyl acetate/cyclohexane (3:7 by volume)], collecting 20-cc fractions. Fractions 4 to 6 are combined and concentrated to dryness under reduced pressure (2.7 kPa) at 40° C. After recrystallization in a mixture of ethyl acetate and diisopropyl ether (1:1 by volume), (5RS, 6SR)-2-(4-chlorophenyl)-6-phenyl-5-phenylcarbamoyloxy-5,6-dihydro-4H-1,3-oxazine (1.36 g), m.p. 167° C., is obtained.

(5RS, 6SR)-2-(4-Chlorophenyl)-6-phenyl-5,6-dihydro-4H-1,3-oxazin-5-ol may be prepared in the following manner: working as in Example 19 for the preparation of (5RS, 6SR)-2-(4-methoxyphenyl)-6-phenyl-5,6-dihydro-4H-1,3-oxazin-5-ol, but starting with (E)-N-cinnamyl-4-chlorobenzamide (4.7 g), after recrystallization in a mixture of ethyl acetate and diisopropyl ether (1:1 by volume), (5RS, 6SR)-2-(4-chlorophenyl)-6-phenyl-5,6-dihydro-4H-1,3-oxazin-5-ol (1.8 g), m.p. 155° C., is obtained.

(E)-N-cinnamyl-4-chlorobenzamide may be prepared in the following manner: oxalyl dichloride (2.6 cc), dissolved in diethyl ether (10 cc), is added dropwise at a temperature in the region of 20° C. to a solution, maintained under an argon atmosphere, of 4-chlorobenzoic acid (4.3 g) and dimethylformamide (0.1 cc) in diethyl ether (40 cc). The solution obtained is stirred for 1 hour 30 minutes at a temperature in the region of 20° C. and then added dropwise to a solution, maintained under an argon atmosphere, of (E)-cinnamylamine (3.3 g) and triethylamine (7 cc) in dichloromethane (50 cc). The suspension is stirred for 30 minutes at a temperature in the region of 30° C. and then poured into distilled water (20 cc). After the precipitate thereby obtained is washed with distilled water, (E)-N-cinnamyl-4-chlorobenzamide (4.7 g), m.p. 143° C. is obtained.

EXAMPLE 21

Phenyl isocyanate (1.43 g) is added at a temperature in the region of 20° C. to a solution, maintained under an argon atmosphere, of (5RS, 6SR)-2-(3-chlorophenyl)-6-phenyl-5,6-dihydro-4H-1,3-oxazin-5-ol (3.55 g) in 1,2-dichloroethane (45 cc). The solution is heated to reflux for 4 hours and then concentrated to dryness under reduced pressure (2.7 kPa). The residue is purified by chromatography on silica (0.063-0.2 mm; 100 g) contained in a column 2.5 cm in diameter [eluent: cyclohexane/ethyl acetate (7:3 by volume)], collecting 20-cc fractions. Fractions 6 to 11 are combined and concentrated to dryness under reduced pressure (2.7 kPa) at 40° C. After recrystallization in diisopropyl ether, (5RS, 6SR)-2-(3-chlorophenyl)-6-phenyl-5-phenylcarbamoyloxy-5,6-dihydro-4H-1,3-oxazine (2.4 g), m.p. 126° C., is obtained.

(5RS, 6SR)-2-(3-Chlorophenyl)-6-phenyl-5,6-dihydro-4H-1,3-oxazin-5-ol may be prepared in the following manner: a 0.47 M solution (49 cc) of 3-chloroperbenzoic acid in dichloromethane is added dropwise at a temperature in the region of 0° C. to a solution, maintained under an argon atmosphere, of (E)-3-chloro-N-cinnamylbenzamide (6.44 g) in dichloromethane (50 cc). The suspension obtained is stirred at a temperature in the region of 0° C. for 2 hours 30 minutes and then filtered. To the filtrate, maintained under an argon atmosphere, boron trifluoride etherate (3.1 cc) is added dropwise at a temperature in the region of 0° C. The mixture is then stirred for 1 hour 30 minutes at a temperature in the region of 20° C. and thereafter added to distilled water (25 cc). The organic phase is separated and then washed successively with 1 N aqueous sodium thiosulphate solution (30 cc), distilled water (30 cc) and saturated aqueous sodium bicarbonate solution (30 cc), dried over magnesium sulphate, filtered and then concentrated to dryness under reduced pressure (2.7 kPa) at 40° C. After recrystallization in diisopropyl ether, (5RS, 6SR)-2-(3-chlorophenyl)-6-phenyl-5,6-dihydro-4H-1,3-oxazin-5-ol (3.55 g), m.p. 142° C., is obtained.

(E)-3-Chloro-N-cinnamylbenzamide may be prepared in the following manner: oxalyl dichloride (4.1 cc), dissolved in diethyl ether (10 cc), is added dropwise at a temperature in the region of 20° C. to a solution, maintained under an argon atmosphere of 3-chlorobenzoic acid (6.8 g) and dimethyl formamide (0.1 cc) in diethyl ether (65 cc). The solution obtained is stirred for 3 hours at a temperature in the region of 20° C. and then added dropwise to a solution, maintained under an argon atmosphere, of (E)-cinnamylamine (5.3 g) and triethylamine (11.2 cc) in dichloromethane (80 cc). The suspension is stirred for 30 minutes at a temperature in the region of 30° C. and thereafter added to distilled water (50 cc). The aqueous phase is acidifed to a pH in the region of 5 with 5 N aqueous hydrochloric acid solution and extracted with dichloromethane (2 × 50 cc). The organic phases are combined, washed with distilled water (2 × 50 cc), dried over magnesium sulphate, filtered and then concentrated to dryness under reduced pressure (2.7 kPa) at 40° C. After recrystallization in a mixture of ethyl acetate and diisopropyl ether (1:16 by volume), (E)-3-chloro-N-cinnamylbenzamide (4.72 g), m.p. 100° C., is obtained.

EXAMPLE 22

Phenyl isocyanate (1 g) is added at a temperature in the region of 20° C. to a solution, maintained under an argon atmosphere, of (5RS, 6SR)-2-(2-fluorophenyl)-6-phenyl-5,6-dihydro-4H-1,3-oxazin-5-ol (2.3 g) in 1,2-dichloroethane (30 cc). The solution obtained is stirred under reflux for 2 hours and then concentrated to dryness under reduced pressure (2.7 kPa). The residue is purified by chromatography on silica (0.063-0.2 mm; 100 g), contained in a column 2.5 cm in diameter [eluent: cyclohexane/ethyl acetate (7:3 by volume)], collecting 20-cc fractions. Fractions 4 to 7 are combined and concentrated to dryness under reduced pressure (2.7 kPa) at 40° C. After recrystallization in ethyl acetate, (5RS, 6SR)-2-(2-fluorophenyl)-6-phenyl-5-phenylcarbamoyloxy-5,6-dihydro-4H-1,3-oxazine (1.3 g), m.p. 128° C., is obtained.

(5RS, 6SR)-2-(2-fluorophenyl)-6-phenyl-5,6-dihydro-4H-1,3-oxazin-5-ol may be prepared in the following manner: a 0.45 M solution (47 cc) of 3-chloroperbenzoic acid in dichloromethane is added dropwise at a temperature in the region of 0° C. to a solution, maintained under an argon atmosphere, of (E)-N-cinnamyl-2-fluorobenzamide (4.8 g) in dichloromethane (45 cc). The suspension obtained is stirred at a temperature in the region of 0° C. for 4 hours and then filtered. To the filtrate, maintained under an argon atmosphere, boron trifluoride etherate (2.7 cc) is added dropwise at a temperature in the region of 0° C. The mixture is then stirred for 2 hours at a temperature in the region of 20° C. and thereafter added to distilled water (25 cc). The organic phase is separated and then washed successively with 1 N aqueous sodium thiosulphate solution (30 cc), distilled water (30 cc) and saturated aqueous sodium bicarbonate solution (30 cc), dried over magnesium sulphate, filtered and then concentrated to dryness under reduced pressure (2.7 kPa) at 40° C. After recrystallization in ethyl acetate, (5RS, 6SR)-2-(2-fluorophenyl)-6-phenyl-5,6-dihydro-4H-1,3-oxazin-5-ol (2.3 g), m.p. 142° C., is obtained.

(E)-N-Cinnamyl-2-fluorobenzamide may be prepared by working in a manner similar to that described in Example 21 for the preparation of (E)-3-chloro-N-cinnamylbenzamide, but starting with (E)-cinnamylamine (5.3 g) and 2-fluorobenzoic acid (6.16 g). After recrystallization in diisopropyl ether, (E)-N-cinnamyl-2-fluorobenzamide (4.8 g), m.p. 68° C., is thereby obtained.

EXAMPLE 23

Phenyl isocyanate (1.7 g) is added at a temperature in the region of 20° C. to a solution, maintained under an argon atmosphere, of (5RS, 6SR)-2-(3,4-dichlorophenyl)-6-phenyl-5,6-dihydro-4H-1,3-oxazin-5-ol (4.7 g) in 1,2-dichloroethane (50 cc). The solution obtained is heated to reflux for 3 hours and then concentrated to dryness under reduced pressure (2.7 kPa). The residue is purified by chromatography on silica (0.063–0.2 mm; 100 g) contained in a column 2.5 cm in diameter [eluent: cyclohexane/ethyl acetate (7:3 by volume)], collecting 20-cc fractions. Fractions 2 to 10 are combined and concentrated to dryness under reduced pressure (2.7 kPa) at 40° C. After recrystallization in diisopropyl ether, (5RS, 6SR)-2-(3,4-dichlorophenyl)-6-phenyl-5-phenylcarbamoyloxy-5,6-dihydro-4H-1,3-oxazine (4 g), m.p. 130° C., is obtained.

(5RS, 6SR)-2-(3,4-Dichlorophenyl)-6-phenyl-5,6-dihydro-4H-1,3-oxazin-5-ol may be prepared in the following manner: a 0.5 M solution (62 cc) of 3-chloroperbenzoic acid in dichloromethane is added dropwise at a temperature in the region of 0° C. to a solution, maintained under an argon atmosphere, of (E)-3,4-dichloro-N-cinnamylbenzamide (9.6 g) in dichloromethane (65 cc). The suspension obtained is stirred at a temperature in the region of 0° C. for 3 hours 30 minutes and then filtered. To the filtrate, maintained under an argon atmosphere, boron trifluoride etherate (3.9 cc) is added dropwise at a temperature in the region of 0° C. The mixture is then stirred for 2 hours at a temperature in the region of 20° C. and thereafter added to distilled water (25 cc). The organic phase is separated and then washed successively with 1 N aqueous sodium thiosulphate solution (30 cc), distilled water (30 cc) and saturated aqueous sodium bicarbonate solution (30 cc), dried over magnesium sulphate, filtered and then concentrated to dryness under reduced pressure (2.7 kPa) at 40° C. After recrystallization in acetonitrile, (5RS, 6SR)-2-(3,4-dichlorophenyl)-6-phenyl-5,6-dihydro-4H-1,3-oxazin-5-ol (4.7 g), m.p. 158° C. is obtained.

(E)-3,4-Dichloro-N-cinnamylbenzamide may be prepared by working in a manner similar to that described in Example 21 for the preparation of (E)-3-chloro-N-cinnamylbenzamide, but starting with (E)-cinnamylamine (5.3 g) and 3,4-dichlorobenzoic acid (8.4 g). After recrystallization in diisopropyl ether, (E)-3,4-dichloro-N-cinnamylbenzamide (9.6 g ), m.p. 105° C., is thereby obtained.

EXAMPLE 24

Phenyl isocyanate (0.92 g) is added at a temperature in the region of 20° C. to a solution, maintained under an argon atmosphere, of (5RS-6SR)-2-(4-fluorophenyl)-6-phenyl-5,6-dihydro-4H-1,3-oxazin-5-ol (2.1 g) in 1,2-dichloroethane (30 cc). The solution obtained is heated to reflux for 4 hours and then concentrated to dryness under reduced pressure (2.7 kPa). The residue is purified by chromatography on silica (0.064–0.2 mm; 100 g) contained in a column 2.5 cm in diameter [eluent: dichloromethane/methanol (98:2 by volume)], collecting 10-cc fractions. Fractions 5 to 15 are combined and concentrated to dryness under reduced pressure (2.7 kPa) at 40° C. (5RS, 6SR)-2-(4-Fluorophenyl)-6-phenyl-5-phenylcarbamoyloxy-5,6-dihydro-4H-1,3-oxazine (1.7 g), m.p. 60° C., is thereby obtained.

(5RS, 6SR)-2-(4-Fluorophenyl)-6-phenyl-5,6-dihydro-4H-1,3-oxazin-5-ol may be prepared in the following manner: a 0.52 M solution (33 cc) of 3-chloroperbenzoic acid in dichloromethane is added dropwise at a temperature in the region of 0° C. to a solution, maintained under an argon atmosphere, of (E)-N-cinnamyl-4-fluorobenzamide (4.5 g) in dichloromethane (36 cc). The suspension is stirred at a temperature in the region of 0° C. for 3 hours 30 minutes and then filtered. To the filtrate, maintained under an argon atmosphere, boron trifluoride etherate (3.9 cc) is added dropwise at a temperature in the region of 0° C. The mixture is then stirred for 1 hour 30 minutes at a temperature in the region of 20° C. and thereafter added to distilled water (25 cc). The organic phase is separated and then washed successively with 1 N aqueous sodium thiosulphate solution, (30 cc), distilled water (30 cc) and saturated aqueous sodium bicarbonane solution (30 cc), dried over magnesium sulphate, filtered and then concentrated to dryness under reduced pressure (2.7 kPa) at 40° C.

The residue is purified by chromatography on silica (0.063–0.2 mm; 100 g) contained in a column 2.5 cm in diameter [eluent: cyclohexane/ethyl acetate (7:3 by volume)], collecting 20-cc fractions. Fractions 9 to 24 are combined and concentrated to dryness under reduced pressure (2.7 kPa) at 40° C. (5RS, 6SR)-2-(4-Fluorophenyl)-6-phenyl-5,6-dihydro-4H-1,3-oxazin-5-ol (2.1 g), m.p. 142° C., is thereby obtained.

(E)-N-Cinnamyl-4-fluorobenzamide may be prepared working in a manner similar to that described in Example 21 for the preparation of (E)-3-chloro-N-cinnamylbenzamide but starting with (E)-cinnamylamine (5.3 g) and 4-fluorobenzoic acid (6.16 g); after recrystallization in a mixture of cyclohexane and ethyl acetate (7:3 by volume), (E)-N-cinnamyl-4-fluorobenzamide (4.7 g), m.p. 122° C., is obtained.

EXAMPLE 25

Phenyl isocyanate (1.1 g) is added at a temperature in the region of 20° C. to a solution, maintained under an argon atmosphere, of (4RS, 5RS)-2,4-diphenyl-5,6-dihydro-4H-1,3-thiazin-5-ol (0.86 g) in 1,2-dichloroethane (10 cc). The solution obtained is stirred under reflux for 3 hours and then concentrated to dryness under reduced pressure (2.7 kPa). The residue is then stirred with a mixture of ethyl acetate and cyclohexane (1:4 by volume). An insoluble precipitate is separated by filtration and the filtrate concentrated to dryness under reduced pressure (2.7 kPa). After recrystallization in diisopropyl ether, (4RS, 5RS)-2,4-diphenyl-5-phenylcarbamoyloxy-5,6-dihydro-4H-1,3-thiazine (0.75 g), m.p. 159° C., is obtained.

(4RS, 5RS)-2,4-diphenyl-5,6-dihydro-4H, 1,3-thiazin-5-ol may be prepared in the following manner: a solution of ethyl azodicarboxylate (1.1 g) dissolved in anhydrous tetrahydrofuran (5 cc) is added dropwise at a temperature in the region of 0° C. to a solution, maintained under an argon atmosphere, of N-[(1RS, 2RS)-2,3-dihydroxy-1-phenylpropyl]thiobenzamide (1.7 g) and triphenylphosphine (1.57 g) in anhydrous tetrahydrofuran (17 cc). The solution obtained is stirred at a temperature in the region of 20° C. for 16 hours and then concentrated to dryness under reduced pressure (2.7 kPa). The residue is purified by chromatography on silica (0.063–0.2 mm; 100 g) contained in a column 2.5 cm in diameter [(eluent: cyclohexane/ethyl acetate (3:7 by volume)], collecting 20-cc fractions. Fractions 5 to 11 are combined and concentrated to dryness under reduced pressure (2.7 kPa) at 40° C. After recrystallization in diisopropyl ether, (4RS, 5RS)-2,4-diphenyl-5,6-dihydro-4H-1,3-thiazin-5-ol (0.86 g), m.p. 142° C. is obtained.

N-[(1RS, 2RS)-2,3-Dihydroxy-1-phenylpropyl)thiobenzamide may be prepared in the following manner. A solution of thiobenzoyl chloride (1 g) in dichloromethane (10 cc) is added dropwise at a temperature in the region of 20° C. to a solution, maintained under an argon atmosphere, of (2RS, 3RS)-3-amino-3-phenyl-1,2-propanediol (1.05 g) and triethylamine (1.76 cc) in dichloromethane (15 cc). The solution is stirred at a temperature in the region of 20° C. for 30 minutes and then hydrolyzed with distilled water (20 cc). The organic phase is washed with distilled water (3×20 cc), dried over magnesium sulphate, filtered, and then concentrated to dryness under reduced pressure (2.7 kPa) at 40° C. The residue is purified by chromatography on silica (0.063–0.2 mm; 100 g) contained in a column 2.5 cm in diameter [eluent: cyclohexane/ethyl acetate (1:1 by volume)], collecting 30-cc fractions. Fractions 6 to 11 are combined and concentrated to dryness under reduced pressure (2.7 kPa) at 40° C. After recrystallization in ethyl acetate, N-[(1RS, 2RS]-2,3-dihydroxyy-1-phenylpropyl]thiobenzamide thiobenzamide (6 g), m.p. 160° C., is obtained.

Thiobenzoyl chloride may be prepared from dithiobenzoic acid according to the method described by H. VIOLA and R. MAYER, Z. Chem., 15, 348, 1975.

Dithiobenzoic acid may be prepared according to the method described by D. F. AYCOCK and G. R. JURCH jr, J. Org. Chem., 44(4), 569, 1979.

EXAMPLE 26

Working in a manner similar to that described in Example 12, but starting with (5RS, 6SR)-6-phenyl-2-(2-thienyl)-5,6-dihydro-4H-1,3-oxazin-5-ol (1.55 g) and phenyl isocyanate (0.8 g), and after recrystallization in isopropanol, (5RS, 6SR)-6-phenyl-5-phenylcarbamoyloxy-2-(2-thienyl)-5,6-dihydro-4H-1,3-oxazine (1.75 g), m.p. 98° C., is obtained.

(5RS, 6SR)-6-Phenyl-2-(2-thienyl)-5,6-dihydro-4H-1,3-oxazin-5-ol may be obtained in the following manner: working as described in Example 22 for the preparation of (5RS, 6SR)-2-(2-fluorophenyl)-6-phenyl-5,6-dihydro-4H-1,3-oxazin-5-ol, but starting with (E)-N-cinnamyl-2-thiophenecarboxamide (5 g), a 0.55 M solution (38 cc) of 3-chloroperbenzoic acid in dichloromethane and boron trifluoride etherate (3.2 g), and after recrystallization in dichloromethane, (5RS, 6SR)-6-phenyl-2-(2-thienyl)-5,6-dihydro-4H-1,3-oxazin-5-ol (2.9 g), m.p. 158° C., is obtained.

(E)-N-Cinnamyl-2-thiophenecarboxamide may be obtained in the following manner: triethylamine (8 g) and then thenoyl chloride (6.5 g) are added to a solution, maintained under a nitrogen atmosphere and at a temperature in the region of 25° C., of (E)-cinnamylamine (5.3 g) in 1,2-dichloroethane (80 cc). The suspension obtained is stirred for 1 hour at a temperature in the region of 25° C. and then poured into water (80 cc). The aqueous phase is acidified to a pH in the region of 5 with 4 N aqueous hydrochloric acid solution and then extracted with 1,2-dichloroethane (2×50 cc). The combined organic phases are washed with water (2×40 cc), dried over magnesium sulphate, filtered and then concentrated to dryness under reduced pressure (4 kPa) at 40° C. The residue is stirred in isopropyl ether (40 cc). The solid is separated by filtration, washed with isopropyl ether (4×10 cc) and dried in the air. (E)-N-Cinnamyl-2-thiophenecarboxamide (5 g), m.p. 110° C., is thereby obtained.

EXAMPLE 27

Working in a manner similar to that described in Example 12, but starting with (5RS, 6SR)-2-(3-furyl)-6-phenyl-5,6-dihydro-4H-1,3-oxazin-5-ol (2.6 g) and phenyl isocyanate (3.8 g), and after purification of the solid obtained by chromatography on a column (height: 30 cm; diameter: 4 cm) of silica (0.2–0.063 mm), eluting with a mixture of dichloroethane and ethyl acetate (90:10 by volume) and collecting 40-cc fractions, fractions 20 to 28 being combined and concentrated to dryness under reduced pressure (4 kPa) at 45° C., followed by recrystallizaiton in isopropyl ether (10 cc), (5RS, 6SR)-2-(3-furyl)-6-phenyl-5-phenylcarbamoyloxy-5,6-dihydro-4H-1,3-oxazine (1.55 g), m.p. 130° C., is obtained.

(5RS, 6SR)-2-(3-Furyl)-6-phenyl-5,6-dihydro-4H-1,3-oxazin-5-ol may be prepared in the following manner: working as in Example 22 for the preparation of (5RS, 6SR)-2-(2-fluorophenyl)-6-phenyl-5,6-dihydro-4H-1,3-oxazin-5-ol, but starting with (E)-N-cinnamyl-3-furancarboxamide (3.8 g), a 0.5 M solution (37 cc) of 3-chloroperbenzoic acid in dichloromethane and boron trifluoride etherate (2.7 g), and after recrystallization in isopropyl ether, (5RS, 6SR)-2-(3-furyl)-6-phenyl-5,6-dihydro-4H-1,3-oxazin-5-ol (2.8 g), m.p. 160° C., is obtained.

(E)-N-Cinnamyl-3-furancarboxamide may be obtained in the following manner: working as in Example 21 for the preparation of (E)-3-chloro-N-cinnamylbenzamide, but starting with 3-furancarboxylic acid (4 g) and (E)-cinnamylamine (4 g), and after recrystallization in isopropyl ether, (E)-N-cinnamyl-3-furancarboxamide (3.9 g), m.p. 115° C. is obtained.

EXAMPLE 28

Working in a manner similar to that described in Example 12, but starting with (5RS, 6SR)-2,6-diphenyl-6-methyl-5,6-dihydro-4H-1,3-oxazin-5-ol (0.8 g) and phenyl isocyanate (1.8 g), and after purification of the solid obtained by chromatography on a column (height: 30 cm; diameter: 2.5 cm) of silica (0.2–0.063 mm), eluting with a mixture of cyclohexane and ethyl acetate (80:20 by volume) and collecting 20cc fractions, fractions 1 to 5 being combined and concentrated to dryness under reduced pressure (4 kPa) at 45° C., followed by recrystallization of the residue in acetonitrile (12 cc), (5RS, 6SR)-6-methyl-2,6-diphenyl-5-phenylcarbamoyloxy-5,6-dihydro-4H-1,3-oxazine (0.95 g), m.p. 180° C., is obtained.

(5RS, 6SR)-6-Methyl-2,6-diphenyl-5,6-dihydro-4H-1,3-oxazin-5-ol may be obtained in the following manner: working as in Example 22 for the preparation of (5RS, 6SR)-2-(2-fluorophenyl)-6-phenyl-5,6-dihydro-4H-1,3-oxazin-5-ol, but starting with (E)-N-(3-phenyl-2-buten-1-yl)benzamide (4.2 g), a 0.35 M solution (48 cc) of 3-chloroperbenzoic acid in dichloromethane and boron trifluoride etherate (2.6 g), and after purification of the oil obtained by chromatography on a column (height: 35 cm; diameter: 3 cm) of silica (0.2–0.063 mm), eluting with a mixture of cyclohexane and ethyl acetate (60:40 by volume) and collecting 30-cc fractions, fractions 9 to 17 being combined and concentrated to dryness under reduced pressure (4 kPa) at 45° C., followed by recrystallization of the residue obtained in isopropyl ether, (5RS, 6SR)-6-methyl-2,6-diphenyl-5,6-dihydro-4H-1,3-oxazin-5-ol (1.65 g, m.p. 130° C.) is obtained.

(E)-N-(3-Phenyl-2-buten-1-yl)benzamide may be prepared in the following manner: working as in Example 26 for the preparation of (E)-N-cinnamyl-2-thiophenecarboxamide, but starting with (E)-3-phenyl-2-butenamine (5 g) and benzoyl chloride (3.8 g) and after recrystallization in acetonitrile, (E)-N-(3-phenyl-2-buten-1-yl)benzamide (2.7 g), m.p. 139° C., is obtained.

(E)-3-Phenyl-2-butenamine may be prepared in the following manner: a solution of 3-phenyl-2-butenenitrile (E/Z mixture, 90:10 mole/mole; 13 g) in anhydrous ethyl ether (100 cc) is poured dropwise into a suspension, maintained under a nitrogen atmosphere and at a temperature in the region of −15° C., of lithium aluminium hydride (3.54 g) in anhydrous diethyl ether (35 cc). The suspension obtained is stirred for 30 minutes at this temperature. Next, water (3.5 cc), 4 N aqueous sodium hydroxide solution (2.7 cc) and then distilled water (12.5 cc) are added and the mixture is stirred for 2 hours at a temperature in the region of 20° C. The insoluble product is separated by filtration. To the ethereal solution, a 3 N ethereal solution (30 cc) of hydrochloric acid is added slowly. The precipitate is separated by filtration, washed with acetonitrile (2×40 cc) and ethyl ether (2×40 cc) and dried in the air. (E)-3-Phenyl-2-butenamine hydrochloride (5.6 g), m.p. 215° C. is thereby obtained. 10 N aqueous sodium hydroxide solution (5 cc) is added to a solution of (E)-3-phenyl-2-butenamine hydrochloride (5.6 g) in distilled water (60 cc), and the oil which comes out of solution is then extracted with diethyl ether (2×60 cc). The ether phases are combined, dried over magnesium sulphate, filtered and then concentrated to dryness under reduced pressure (4 kPa) at 30° C. (E)-3-Phenyl-2-butenamine (3.65 g) is obtained in the form of an orange-coloured oil.

3-Phenyl-2-butenenitrile (E/Z mixture, 90:10 mole/mole) may be prepared according to the method described by F. TEXIER-BOULLET and A. FOUCAUD, Synthesis, 884, 1979.

EXAMPLE 29

Working in a manner similar to that described in Example 12, but starting with 4-methyl-2,6-diphenyl-5,6-dihydro-4H-1,3-oxazin-5-ol (mixture of 4SR, 5RS, 6SR and 4RS, 5RS, 6SR diastereoisomers, 50:50 mole/mole; 3.7 g) and phenyl isocyanate (5 g), then purifying the oil obtained by chromatography on a column (height: 45 cm; diameter: 4 cm) of silica, eluting with a mixture of cyclohexane and ethyl acetate (85:15 by volume) and collecting 25-cc fractions, fractions 22 to 25 being combined and concentrated to dryness under reduced pressure (4 kPa) at 45° C., followed by recrystallization of the solid obtained in acetonitrile, (4SR, 5RS, 6SR)-2,6-diphenyl-4-methyl-5-phenylcarbamoyloxy-5,6-dihydro-4H-1,3-oxazine (0.8 g), m.p. 150° C., is obtained.

Fractions 28 to 30 are combined and concentrated to dryness under reduced pressure (4 kPa) at 45° C. The solid obtained is recrystallized in acetonitrile to give (4RS, 5RS, 6SR)-2,6-diphenyl-4-methyl-5-phenylcarbamoyloxy-5,6-dihydro-4H-1,3-oxazine (0.1 g), m.p. 195° C.

4-Methyl-2,6-diphenyl-5,6-dihydro-4H-1,3-oxazin-5-ol (mixture of 4SR, 5RS, 6SR and 4RS, 5RS, 6SR diastereoisomers, 50:50 mole/mole) may be obtained in the following manner: working as in Example 22 for the preparation of (5RS, 6SR)-2-(2-fluorophenyl)-6-phenyl-5,6-dihydro-4H-1,3-oxazin-5-ol, but starting with N-[(RS, E)-4-phenyl-3-buten-2-yl]benzamide (4.3 g), a 0.5 M solution (34.5 cc) of 3-chloroperbenzoic acid in dichloromethane and boron trifluoride etherate (2.7 g), 4-methyl-2,6-diphenyl-5,6-dihydro-4H-1,3-oxazin-5-ol (mixture of 4SR, 5RS, 6SR and 4RS, 5RS, 6SR diastereoisomers, 50:50 mole/mole; 3.8 g), m.p. 60° C., is obtained.

N-[(RS, E)-4-Phenyl-3-buten-2-yl]benzamide may be prepared in the following manner: working as in Example 26 for the preparation of (E)-N-cinnamyl-2-thiophenecarboxamide, but starting with (RS, E)-4-phenyl-3-buten-2-ylamine (4.6 g) and benzoyl chloride (5.3 g), and after the residue is stirred in isopropyl ether, N-[(RS, E)-4-phenyl-3-buten-2-yl]benzamide (4.3 g), m.p. 135° C., is obtained.

(RS, E)-4-Phenyl-3-buten-2-ylamine may be prepared according to the method described by T. G. SCHENCK and B. BOSNICH, J. Am. Chem. Soc., 107(7),2064, 1985.

EXAMPLE 30

3,4-Methylenedioxyaniline (0.55 g) is added at a temperature in the region of 20° C. to a solution, maintained under an argon atmosphere, of (4RS, 5RS)-5-(4-nitrophenoxycarbonyloxy)-2,4-diphenyl-5,6-dihydro-4H-1,3-oxazine (0.84 g) and 4-(dimethylamino)pyridine (0.15 g) in acetonitrile (25 cc). The solution obtained is heated to reflux for 3 hours and then concentrated to dryness under reduced pressure (2.7 kPa). The residue is purified by chromatography on silica (0.063-0.2 mm; 30 g) contained in a column 1 cm in diameter, collecting 20-cc fractions. Fractions 1 to 8, eluted with a mixture of ethyl acetate and cyclohexane (3:7 by volume), are combined and concentrated to dryness under reduced pressure (2.7 kPa) at 40° C. After recrystallization in a mixture of acetonitrile and diisopropyl ether (1:9 by volume), (4RS, 5RS)-5-(3,4-methylenedioxyphenylcarbamoyloxy)-2,4-diphenyl-5,6-dihydro-4H-1,3-oxazine (0.49 g), m.p. 163° C. is obtained.

(4RS, 5RS)-5-(4-Nitrophenoxycarbonyloxy)-2,4-diphenyl-5,6-dihydro-4H-1,3-oxazine may be prepared in the following manner: 4-nitrophenyl chloroformate (24 g) is added at a temperature in the region of 0° C. to a solution, maintained under an argon atmosphere of (4RS, 5RS)-2,4-diphenyl-5,6-dihydro-4H-1,3-oxazin-5-ol (15.2 g) in pyridine (100 cc). The solution obtained is stirred for 16 hours at a temperature in the region of 20° C. and then poured into distilled water (750 cc). The mixture is extracted with dichloromethane (3×200 cc). The organic phases are combined, washed with distilled water (2×100 cc), dried over magnesium sulphate, filtered and then concentrated to dryness under reduced pressure (2.7 kPa) at 40° C. The oily residue is purified by chromatography on silica (0.063-0.2 mm; 400 g) contained in a column 7 cm in diameter, collecting 25-cc fractions. Fractions 1 to 15, eluted with a mixture of ethyl acetate and cyclohexane (3:7 by volume), are concentrated to dryness under reduced pressure (2.7 kPa) at 40° C. After recrystallization in a mixture of ethyl acetate and diisopropyl ether (4:1 by volume), (4RS, 5RS)-5-(4-nitrophenoxycarbonyloxy)-2,4-diphenyl-5,6-dihydro-4H-1,3-oxazine (18.5 g), m.p. 126° C., is obtained.

EXAMPLE 31

3,4-Methylenedioxyaniline (1.1 g) is added at a temperature in the region of 20° C. to a solution, maintained under an argon atmosphere, of (5RS, 6SR)-5-(4-nitrophenoxycarbonyloxy)-2,6-diphenyl-5,6-dihydro-4H-1,3-oxazine (1.67 g) and 4-(dimethylamino)pyridine (0.2 g) in anhydrous acetonitrile (50 cc). The solution obtained is heated to reflux for 5 hours and then concentrated to dryness under reduced pressure (2.7 kPa). The oil obtained is purified by chromatography on silica (0.063–0.2 mm; 50 g) contained in a column 2 cm in diameter [eluent: cyclohexane/ethyl acetate/triethylamine (65:30:5 by volume)], collecting 15-cc fractions. Fractions 3 to 6 are combined and concentrated to dryness under reduced pressure (2.7 kPa) at 40° C. After recrystallization in diisopropyl ether, (5RS, 6SR)-5-(3,4-methylenedioxyphenylcarbamoyloxy)-2,6-diphenyl-5,6-dihydro-4H-1,3-oxazine (0.8 g), m.p. 138° C., is obtained.

(5RS, 6SR)-5-(4-Nitrophenoxycarbonyloxy)-2,6-diphenyl-5,6-dihydro-4H-1,3-oxazine may be prepared in the following manner: 4-nitrophenyl chloroformate (36 g) is added at a temperature in the region of 0° C. to a solution, maintained under an argon atmosphere, of (5RS, 6SR)-2,6-diphenyl-5,6-dihydro-4H-1,3-oxazin-5-ol (30.3 g) in anhydrous pyridine (300 cc). The solution obtained is stirred for 16 hours at a temperature in the region of 20° C. and then poured into distilled water (2000 cc). The mixture is extracted with dichloromethane (3×500 cc). The organic phases are combined, washed with distilled water (3×400 cc), dried over magnesium sulphate, filtered and then concentrated to dryness under reduced pressure (2.7 kPa) at 40° C. After recrystallization in a mixture of ethyl acetate and diisopropyl ether (3:2 by volume), (5RS, 6SR)-5-(4-nitrophenoxycarbonyloxy)-2,6-diphenyl-5,6-dihydro-4H-1,3-oxazine (30 g), m.p. 160° C. is obtained.

EXAMPLE 32

3,4-Dimethylaniline (1.7 g) is added at a temperature in the region of 20° C. to a solution, maintained under an argon atmsophere, of (5RS, 6SR)-5-(4-nitrophenoxycarbonyloxy)-2,6-diphenyl-5,6-dihydro-4H-1,3-oxazine (3 g) and 4-(dimethylamino)pyridine (0.3 g) in anhydrous acetonitile (100 cc). The solution obtained is heated to reflux for 4 hours and then concentrated to dryness under reduced pressure (2.7 kPa). The residue is purified by chromatography on silica (0.063–0.2 mm; 50 g) contained in a column 2 cm in diameter [eluent: cyclohexane/ethyl acetate/triethylamine (65:30:5 by volume)], collecting 25-cc fractions. Fractions 2 to 6 are combined and concentrated to dryness under reduced pressure (2.7 kPa) at 40° C. (5RS, 6SR)-5-(3,4-Dimethylphenylcarbamoyloxy)-2,6-diphenyl-5,6-dihydro-4H-1,3-oxazine (1 g), m.p. 80° C., is thereby obtained.

EXAMPLE 33 meta-Anisidine (1.72 g) is added at a temperature in the region of 20° C. to a solution, maintained under an argon atmosphere, of (5RS, 6SR)-5-(4-nitrophenoxycarbonyloxy)-2,6-diphenyl-5,6-dihydro-4H-1,3-oxazine (3 g) and 4-(dimethylamino)pyridine (0.3 g) in anhydrous N,N-dimethylformamide (50 cc). The solution obtained is heated to a temperature in the region of 70° C. for 6 hours and then concentrated to dryness under reduced pressure (2.7 kPa). The residue is purified by chromatography on silica (0.063–0.2 mm; 50 g) contained in a column 2 cm in diameter [eluent: cyclohexane/ethyl acetate/triethylamine (65:30:5 by volume)], collecting 25-cc fractions. Fractions 2 to 5 are combined and concentrated to dryness under reduced pressure (2.7 kPa) at 40° C. After recrystallization in diisopropyl ether, (5RS, 6SR)-5-(3-methoxyphenylcarbamoyloxy)-2,6-diphenyl-5,6-dihydro-4H-1,3-oxazine (1.8 g), m.p. 110° C. is obtained.

EXAMPLE 34

Working in a manner similar to that described in Example 33, but starting with (5RS, 6SR)-5-(4-nitrophenoxycarbonyloxy)-2,6-diphenyl-5,6-dihydro-4H-1,3-oxazine (3 g) and 3-nitroaniline (1.9 g) and after recrystallization in a mixture of acetonitrile and diisopropyl ether (1:1 by volume), (5RS, 6SR)-5-(3-nitrophenylcarbamoyloxy)-2,6-diphenyl-5,6-dihydro-4H-1,3-oxazine (0.85 g), m.p. 176° C., is obtained.

EXAMPLE 35

3,4-Methylenedioxyaniline (0.82 g) is added at a temperature in the region of 20° C. to a solution, maintained under an argon atmosphere, of (4RS, 5RS)-2-(4-methoxyphenyl)-5-(4-nitrophenoxycarbonyloxy)-4-phenyl-5,6-dihydro-4H-1,3-oxazine (1.34 g) and 4(dimethylamino)pyridine (0.1 g) in anhydrous acetonitrile (30 cc). The solution obtained is heated to reflux for 4 hours and then concentrated to dryness under reduced pressure (2.7 kPa). The residue is purified by chromatography on silica (0.063–0.2 mm; 30 g) contained in a column 2 cm in diameter [eluent: cyclohexane/ethyl acetate/triethylamine (65:35:5 by volume)], collecting 25-cc fractions. Fractions 2 to 5 are combined and concentrated to dryness under reduced pressure (2.7 kPa) at 40° C. After recrystallization in a mixture of ethyl acetate and diisopropyl ether (1:2 by volume), (4RS, 5RS)-2-(4-methoxyphenyl)-5-(3,4-methylenedioxyphenylcarbamoyloxy)-4-phenyl-5,6-dihydro-4H-1,3-oxazine (1.4 g), m.p. 160° C. is obtained.

(4RS, 5RS)-2-(4-Methoxyphenyl)-5-(4-nitrophenoxycarbonyloxy)-4-phenyl-5,6-dihydro-4H-1,3-oxazine may be prepared in the following manner: 4-nitrophenyl chloroformate (6.4 g) is added at a temperature in the region of 0° C. to a solution, maintained under an argon atmosphere of (4RS, 5RS)-2-(4-methoxyphenyl)-4-phenyl-5,6-dihydro-4H-1,3-oxazin-5-ol (6 g) in anhydrous pyridine (75 cc). The solution obtained is stirred for 5 hours at a temperature in the region of 20° C. and then poured into distilled water (400 cc). The mixture is extracted with dichloromethane (3×250 cc). The organic phases are combined, washed with distilled water (3×150 cc), dried over magnesium sulphate, filtered and then concentrated to dryness under reduced pressure (2.7 kPa) at 40° C. After recrystallization in ethyl acetate, (4RS, 5RS)-2-(4-methoxyphenyl)-5-(4-nitrophenoxycarbonyloxy)-4-phenyl-5,6-dihydro-4H-1,3-oxazine (5 g), m.p. 164° C., is obtained.

EXAMPLE 36

Phenyl isocyanate (1.6 g) is added at a temperature in the region of 20° C. to a solution, maintained under an argon atmosphere, o[(5RS, 6SR)-2-(4-nitrophenyl)-6-phenyl-5,6-dihydro-4H-1,3-oxazin-5-ol (4.1 g) in 1,2-dichloroethane (45 cc). The solution obtained is heated to reflux for 4 hours and then concentrated to dryness under reduced pressure (2.7 kPa). The residue is purified by chromatography on silica (0.063–0.2 mm; 100 g) contained in a column 2.5 cm in diameter [eluent: dichloromethane/methanol (97:3 by volume)], collecting 20-cc fractions. Fractions 10 to 31 are combined and concentrated to dryness under reduced pressure (2.7 kPa) at 40° C. After recrystallization in acetonitrile, (5RS, 6SR)-2-(4-nitrophenyl)-6-phenyl-5-phenylcarbamoyloxy-5,6-dihydro-4H-1,3-oxazine (1.35 g), m.p. 170° C., is obtained.

(5RS, 6SR)-2-(4-Nitrophenyl)-6-phenyl-5,6-dihydro-4H-1,3-oxazin-5-ol may be prepared in the following manner: a 0.48 M solution (45 cc) of 3-chloroperbenzoic acid in dichloromethane is added dropwise at a temperature in the region of 0° C. to a solution, maintained under an argon atmosphere, of (E)-N-cinnamyl-4-nitrobenzamide (5.6 g) in dichloromethane (45 cc). The suspension obtained is stirred at a temperature in the region of 0° C. for 1 hour and then filtered To the filtrate, maintained under an argon atmosphere, boron trifluoride etherate (2.5 cc) is added dropwise at a temparature in the region of 0° C. The mixture is then stirred for 2 hours 30 minutes at a temperature in the region of 20° C. and thereafter poured into distilled water (100 cc). The organic phase is separated and then washed successively with 1 N aqueous sodium thiosulphate solution (30 cc), distilled water (30 cc) and saturated aqueous sodium bicarbonate solution (30 cc), dried over magnesium sulphate, filtered and then concentrated to dryness under reduced pressure (2.7 kPa) at 40° C. (5RS, 6SR)-2-(4-Nitrophenyl)-6-phenyl-5,6-dihydro-4H-1,3-oxazin-5-ol (4.4 g), m.p. 148° C., is thereby obtained.

(E)-N-Cinnamyl-4-nitrobenzamide may be prepared according to the method described by S. P. McMANUS, Don W. WARE, A. RANDY, J. Org. Chem., 43(22), 4288, 1978.

EXAMPLE 37

Phenyl isocyanate (0.61 g) is added at a temperature in the region of 20° C. to a solution, maintained under an argon atmosphere, of (5RS, 6SR)-2-(4-methylphenyl)-6-phenyl-5,6-dihydro-4H-1,3-oxazin-5-ol (1.4 g) in 1,2-dichloroethane (20 cc). The solution obtained is heated to reflux for 5 hours and then concentrated to dryness under reduced pressure (2.7 kPa). The residue is purified by chromatography on silica (0.063–0.2 mm; 50 g) contained in a column 2.5 cm in diameter [eluent: dichloromethane/methanol (9:1 by volume)], collecting 20-cc fractions. Fractions 7 to 17 are combined and concentrated to dryness under reduced pressure (2.7 kPa) at 40° C. (5RS, 6SR)-2-(4-Methylphenyl)-6-phenyl-5-phenylcarbamoyloxy-5,6-dihydro-4H-1,3-oxazine (0.7 g), m.p. 138° C., is obtained.

(5RS, 6SR)-2-(4-Methylphenyl)-6-phenyl-5,6-dihydro-4H-1,3-oxazin-5-ol may be prepared in the following manner: a 0.45 M solution (41 cc) of 3-chloroperbenzoic acid in dichloromethane is added dropwise at a temperature in the region of 0° C. to a solution, maintained under an argon atmosphere, of (E)-N-cinnamyl-4-methylbenzamide (4.2 g) in dichloromethane (40 cc). The suspension obtained is stirred at a temperature in the region of 0° C. for 2 hours and then filtered. To the filtrate, maintained under an argon atmosphere, boron trifluoride etherate (2.1 cc) is added dropwise at a temperature in the region of 0° C. The mixture is then stirred for 2 hours at a temperature in the region of 20° C. and thereafter poured into distilled water (100 cc). The organic phase is separated and then washed successively with 1 N aqueous sodium thiosulphate solution (30 cc), distilled water (30 cc) and saturated aqueous sodium bicarbonate solution (30 cc), dried over magnesium sulphate, filtered and then concentrated to dryness under reduced pressure (2.7 kPa) at 40° C. The residue is purified by chromatography on silica (0.063–0.2 mm; 50 g) contained in a column 2.5 cm in diameter [eluent: dichloromethane/methanol (98:2 by volume)], collecting 20-cc fractions. Fractions 19 to 25 are combined and concentrated to dryness under reduced pressure (2.7 kPa) at 40° C. After recrystallization in ethyl acetate, (5RS, 6SR)-2-(4-methylphenyl)-6-phenyl-5,6-dihydro-4H-1,3-oxazin-5-ol (1.4 g), m.p. 168° C., is obtained.

(E)-N-cinnamyl-4-methylbenzamide may be prepared by working in a manner similar to that described in Example 21 for the preparation of (E)-3-chloro-N-cinnamylbenzamide but starting with cinnamylamine (5.3 g) and 4-methylbenzoic acid (6 g). After recrystallization in ethyl acetate, (E)-N-cinnamyl-4-methylbenzamide (4.2 g), m.p. 134° C., is thereby obtained.

EXAMPLE 38

Phenyl isocyanate (0.49 g) is added at a temperature in the region of 20° C. to a solution, maintained under an argon atmosphere, of (5RS, 6SR)-2-[4-(dimethylamino)-phenyl]-6-phenyl-5,6-dihydro-4H-1,3-oxazin-5-ol (1 g) in 1,2-dichloroethane (12 cc). The solution obtained is heated to reflux for 2 hours and then concentrated to dryness under reduced pressure (2.7 kPa), The residue is purified by chromatography on silica (0.063–0.02 mm; 50 g) contained in a column 2.5 cm in diameter (eluent: cyclohexane/ethyl acetate (7:3 by volume)]collecting 20-cc fractions. Fractions 9 to 15 are combined and concentrated to dryness under reduced pressure (2.7 kPa) at 40° C. After recrystallization in diethyl ether, (5RS, 6SR)-2-[4-(dimethylamino)phenyl]-6-phenyl-5-phenylcarbamoyloxy-5,6-dihydro-4H-1,3-oxazine (0.55 g), m.p. 183° C., is obtained.

(5RS, 6SR)-2-[4-(Dimethylamino)phenyl]-6-phenyl-5,6-dihydro-4H-1,3-oxazin-5-ol may be prepared in the following manner: boron trifluoride etherate (1.3 cc), dissolved in dichloromethane (3 cc), is added dropwise at a temperature in the region of 0° C. to a solution, maintained under an argon atmosphere, of N-[(2RS, 3RS)-2,3-epoxy-3-phenylpropyl]-4-(dimethylamino)-benzamide (2.8 g) in dichloromethane (65 cc). The solution obtained is then stirred for 1 hour at a temperature in the region of 20° C. and thereafter treated with 1 N aqueous sodium hydroxide solution (11 cc), stirring being maintained for 30 minutes. The aqueous phase is separated and then reextracted with dichloromethane (2×50 cc). The organic phases are combined, dried over magnesium sulphate, filtered and then concentrated to dryness under reduced pressure (2.7 kPa) at 40° C. The residue is purified by chromatography on silica (0.063–0.2 mm; 200 g) contained in a column 3 cm in diameter (eluent: ethyl acetate), collecting 35-cc fractions. Fractions 6 to 31 are combined and concentrated to dryness under reduced pressure (2.7 kPa) at 40° C. (5RS, 6SR)-2-[4-Dimethylamino)phenyl]-6-phenyl-5,6-dihydro-4H-1,3-oxazin-5-ol (1.23 g), m.p. 172° C., is thereby obtained.

N-[(2RS, 3RS)-2,3-epoxy-3-phenylpropyl]-4-(dimethylamino)benzamide may be prepared in the following manner:

a—Preparation of the solution A:

Carbonyldiimidazole (3.24 g) is added dropwise at a temperature in the region of 0° C. to a solution, maintained under an argon atmosphere, of 4-(dimethylamino)benzoic acid (3.3 g) in dichloromethane (60 cc). The solution obtained (solution A) is then stirred for 2 hours at a temperature in the region of 20° C. while the solution B is prepared.

b—Preparation of the solution B:

N-[(2RS, 3RS)-2,3-epoxy-3-phenylpropyl]-trifluoroacetamide (4.9 g) is added to 3.57 N aqueous potassium hydroxide solution (6 cc). After 7 minutes' stirring at a temperature in the region of 20° C., the solution obtained is saturated with sodium chloride and then extracted with dichloromethane (2×50 cc). The organic phases are combined, dried over magnesium sulphate and then filtered, thereby forming a methylene chloride solution of (2RS, 3RS)-2,3-epoxy-3-phenylpropanamine (solution B).

The solution B is added dropwise to the solution A. The solution obtained is then stirred for 3 hours at a temperature in the region of 20° C. and thereafter poured into distilled water (100 cc). The aqueous phase is separated and then re-extracted with dichloromethane (2×50 cc). The organic phases are combined, washed with saturated aqueous sodium chloride solution, dried over magnesium sulphate, filtered and then concentrated to dryness under reduced pressure (2.7 kPa) at 40° C. After recrystallization in a mixture of ethyl acetate and diisopropyl ether (2:1 by volume), N-[(2RS, 3RS)-2,3-epoxy-3-phenylpropyl]-4-(dimethylamino)benzamide (2.95 g), m.p. 127° C., is obtained.

N-[(2RS, 3RS)-2,3-epoxy-3-phenylpropyl]trifluoroacetamide may be prepared in the following manner: a 0.425 M solution (180 cc) of 3-chloroperbenzoic acid in dichloromethane is added dropwise at a temperature in the region of 0° C. to a solution, maintained under an argon atmosphere, of (E)-N-cinnamyltrifluoroacetamide (17 g) in dichloromethane (150 cc). The suspension obtained is stirred at a temperature in the region of 20° C. for 6 hours, cooled to a temperature in the region of 0° C. and then filtered. The filtrate is washed successively with 1 N aqueous sodium thiosulphate solution (200 cc), distilled water (200 cc) and saturated aqueous sodium bicarbonate solution (200 cc), dried over magnesium sulphate, filtered and then concentrated to dryness under reduced pressure (2.7 kPa) at 40° C. N-[(2RS, 3RS)-2,3-Epoxy-3-phenylpropyl]trifluoroacetamide (18 g), m.p. 79° C., is thereby obtained (E)-N-Cinnamyl trifluoroacetamide may be prepared according to the method described by P. HODGE et al., Synthesis, 1984, 941.

EXAMPLE 39

Phenyl isocyanate (0.72 g) is added at a temperature in the region of 20° C. to a solution, maintained under an argon atmosphere, of (5RS, 6SR)-2-(4-acetamidophenyl)-6-phenyl-5,6-dihydro-4H-1,3-oxazin-5-ol (1.55 g) in 1,2-dichloroethane (20 cc). The solution obtained is heated to 80° C. for 50 hours and then concentrated to dryness under reduced pressure (2.7 kPa). The solid obtained is purified by chromatography on silica (0.063–0.2 mm; 100 g) contained in a column 2.5 cm in diameter, collecting 30-cc fractions. Fractions 8 to 15 are eluted with a mixture of ethyl acetate and cyclohexane (3:2 by volume) and then concentrated to dryness under reduced pressure (2.7 kPa) at 40° C. After recrystallization in ethyl acetate, (5RS, 6SR)-2-(4-acetamidophenyl)-6-phenyl-5-phenylcarbamoyloxy-5,6-dihydro-4H-1,3-oxazine (1.25 g), melting between 214° and 220° C., is obtained.

(5RS, 6SR)-2-(4-Acetamidophenyl)-6-phenyl-5,6-dihydro-4H-1,3-oxazin-5-ol may be prepared in the following manner: boron trifluoride etherate (2 cc), dissolved in dichloromethane (5 cc), is added dropwise at a temperature in the region of 0° C. to a solution, maintained under an argon atmosphere, of N-[(2RS, 3RS)-2,3-epoxy-3-phenylpropyl]-4-acetamidobenzamide (4.5 g) in dichloromethane (80 cc). The solution obtained is then stirred for 30 minutes at a temperature in the region of 20° C. and thereafter treated with 1 N aqueous sodium hydroxide solution (16 cc), stirring being maintained for 30 minutes. The aqueous phase is separated and then re-extracted with ethyl acetate (2×50 cc). The organic phases are combined, dried over magnesium sulphate, filtered and then concentrated to dryness under reduced pressure (2.7 kPa) at 40° C. After recrystallization in a mixture of petroleum ether and ethanol (95:5 by volume), (5RS, 6SR)-2-(4-acetamidophenyl)-6-phenyl-5,6-dihydro-4H-1,3-oxazin-5-ol (2 g), m.p. 220° C., is obtained.

N-[(2RS, 3RS)-2,3-Epoxy-3-phenylpropyl]-4-acetamidobenzamide may be prepared in the following manner:

a—Preparation of solution A:

Carbonyldiimidazole (6.5 g) is added in small portions at a temperature in the region of 0° C. to a solution, maintained under an argon atmosphere, of 4-acetamidobenzoic acid (7 g) in dichloromethane (80 cc). The solution obtained (solution A) is then stirred for 2 hours at a temperature in the region of 20° C. while the solution B is prepared.

b—Preparation of the solution B:

N-[(2RS, 3RS)-2,3-Epoxy-3-phenylpropyl]trifluoroacetamide (11 g) is added to 3.6 N aqueous potassium hydroxide solution (12.5 cc). After 7 minutes' stirring at a temperature in the region of 20° C., the solution obtained is saturated with sodium chloride and then extracted with dichloromethane (2×100 cc). The organic phases are combined, dried over magnesium sulphate and then filtered, thereby forming a methylene chloride solution of (2RS, 3RS)-2,3-epoxy-3-phenylpropanamine (solution B).

The solution B is added dropwise to the solution A. The solution obtained is then stirred for 3 hours at a temperature in the region of 20° C. and thereafter poured into distilled water (100 cc). The aqueous phase is separated and then re-extracted with dichloromethane (2×50 cc). The organic phases are combined, washed with saturated aqueous sodium chloride solution, dried over magnesium sulphate, filtered and then concentrated to dryness under reduced pressure (2.7 kPa) at 40° C. After recrystallization in ethyl acetate, N-[(2RS, 3RS)-2,3-epoxy-3-phenylpropyl]-4-acetamidobenzamide (4.8 g) is obtained.

EXAMPLE 40

Phenyl isocyanate (0.38 g) is added at a temperature in the region of 20° C. to a solution, maintained under an argon atmosphere, of (5RS, 6SR)-2-(4-ethoxyphenyl)-6-phenyl-5,6-dihydro-4H-1,3-oxazin-5-ol (0.8 g) in 1,2-dichloroethane (10 cc). The solution obtained is heated to 80° C. for 3 hours and then concentrated to dryness under reduced pressure (2.7 kPa). The solid obtained is purified by chromatography on silica (0.063–0.2 mm; 100 g), contained in a column 2 cm in diameter, collecting 20-cc fractions. Fractions 3 and 4, eluted with a mixture of cyclohexane and ethyl acetate (6:4 by volume), are concentrated to dryness under reduced pressure (2.7 kPa) at 40° C. The solid obtained is then purified again by chromatography on silica (0.063-0.2 mm; 100 g), contained in a column 2 cm in diameter, collecting 20-cc fractions. Fractions 5 to 10, eluted with a mixture of cyclohexane, ethyl acetate and triethylamine (65:30:5 by volume), are concentrated to dryness under reduced pressure (2.7 kPa) at 40° C. After recrystallization in ethyl acetate, (5RS, 6SR)-2-(4-ethoxyphenyl)-6-phenyl-5-phenylcarbamoyloxy-5,6-dihydro-4H-1,3-oxazine (0.35 g), m.p. 80° C., is obtained.

(5RS, 6SR)-2-(4-Ethoxyphenyl)-6-phenyl-5,6-dihydro-4H-1,3-oxazin-5-ol may be prepared in the following manner: a 0.43 M solution (46.5 cc) of 3-chloroperbenzoic acid in dichloromethane is added dropwise at a temperature in the region of 0° C. to a solution, maintained under an argon atmosphere, of (E)-4-ethoxy-N-cinnamylbenzamide (5.7 g) in dichloromethane (75 cc). The suspension obtained is stirred at a temperature in the region of 20° C. for 2 hours and then filtered. To the filtrate obtained and maintained under an argon atmosphere, boron trifluoride etherate (26 cc) is added dropwise at a temperature in the region of 0° C. The mixture is then stirred for 2 hours at a temperature in the region of 20° C. and thereafter added to distilled water (50 cc). The organic phase is separated and then washed successively with 1 N aqueous sodium thiosulphate solution (30 cc), distilled water (30 cc) and saturated aqueous sodium bicarbonate solution (30 cc), dried over magnesium sulphate, filtered and then concentrated to dryness under reduced pressure (2.7 kPa) at 40° C. The oil obtained is purified by chromatography on silica (0.063-0.2 mm; 200 g) contained in a column 2.5 cm in diameter, collecting 25-cc fractions. Fractions 12 to 20, eluted with a mixture of cyclohexane and ethyl acetate (1:1 by volume), are concentrated to dryness under reduced pressure (2.7 kPa) at 40° C. After recrystallization in ethyl acetate, (5RS, 6SR)-2-(4-ethoxyphenyl)-6-phenyl-5,6-dihydro-4H-1,3-oxazin-5-ol (0.8 g), m.p. 124° C., is obtained.

(E)-4-Ethoxy-N-cinnamylbenzamide may be prepared in the following manner: working as in Example 21 for the preparation of (E)-3-chloro-N-cinnamylbenzamide, but starting with cinnamylamine (6.6 g) and 4-ethoxybenzoic acid (8.3 g), and after recrystallization in ethyl acetate, (E)-4-ethoxy-N-cinnamylbenzamide (8.4 g), m.p. 132° C., is obtained.

EXAMPLE 41

Phenyl isocyanate (0.79 g) is added at a temperature in the region of 20° C. to a solution, maintained under an argon atmosphere, of (5RS, 6SR)-2-[4-(methylthio)phenyl]-6-phenyl-4H-1,3-oxazin-5-ol (1.8 g) in 1,2-dichloroethane (25 cc). The solution obtained is heated to 80° C. for 4 hours and then concentrated to dryness under reduced pressure (2.7 kPa). After recrystallization in acetonitrile, (5RS, 6SR)-2-[4-(methylthio)phenyl]-6-phenyl-5-phenylcarbamoyloxy-5,6-dihydro-4H-1,3-oxazine (1 g), m.p. 170° C., is obtained.

(5RS, 6SR)-2-[4-(Methylthio)phenyl]-6-phenyl-5,6-dihydro-4H-1,3-oxazin-5-ol may be prepared in the following manner: boron trifluoride etherate (1.9 cc), dissolved in dichloromethane (5 cc), is added dropwise at a temperature in the region of 0° C. to a solution, maintained under an argon atmosphere, of N-[(2RS, 3RS)-2,3-epoxy-3-phenylpropyl]-4-(methylthio)benzamide (4.2 g) in dichloromethane (50 cc). The solution obtained is then stirred for 3 hours at a temperature in the region of 20° C. and thereafter treated with 1 N aqueous sodium hydroxide solution (15 cc), stirring being maintained for 30 minutes. The aqueous phase is separated and then re-extracted with dichloromethane (2 × 50 cc). The organic phases are combined, dried over magnesium sulphate, filtered and then concentrated to dryness under reduced pressure (2.7 kPa) at 40° C. After recrystallization in acetonitrile, (5RS, 6SR)-2-[-4-(methylthio)phenyl]-6-phenyl-5,6-dihydro-4H-1,3-oxazin-5-ol (1.8 g), m.p. 130° C., is obtained.

N-[(2RS, 3RS)-2,3-Epoxy-3-phenylpropyl]-4-(methylthio)benzamide may be prepared in the following manner:

a—Preparation of the solution A:

Carbonyldiimidazole (9.7 g) is added in small portions at a temperature in the region of 0° C. to a solution, maintained under an argon atmosphere, of 4-(methylthio)benzoic acid (10 g) in dichloromethane (150 cc). The solution obtained (solution A) is then stirred for 2 hours at a temperature in the region of 20° C. while the solution B is prepared.

b—Preparation of the solution B:

N-[(2RS, 3RS)-2,3-Epoxy-3-phenylpropyl]trifluoroacetamide (9.8 g) is added to 3.1 N aqueous potassium hydroxide solution (13 cc). After 7 minutes' stirring at a temperature in the region of 20° C., the solution obtained is saturated with sodium chloride and then extracted with dichloromethane (2 × 100 cc). The organic phases are combined, dried over magnesium sulphate and then filtered, thereby forming a methylene chloride solution of (2RS, 3RS)-2,3-epoxy-3phenylpropanamine (solution B).

The solution B is added dropwise to the solution A. The solution obtained is then stirred for 3 hours at a temperature in the region of 20° C. and thereafter poured into distilled water (100 cc). The aqueous phase is separated and then re-extracted with dichloromethane (2 × 50 cc). The organic phases are combined, washed with saturated aqueous sodium chloride solution, dried over magnesium sulphate, filtered and then concentrated to dryness under reduced pressure (2.7 kPa) at 40° C. After recrystallization in ethyl acetate, N-[(2RS, 3RS)-2,3-epoxy-3-phenylpropyl]-4-(methylthio)benzamide (4.2 g), m.p. 110° C., is obtained.

EXAMPLE 42

Phenyl isocyanate (0.95 g) is added at a temperature in the region of 20° C. to a solution, maintained under an argon atmosphere, of (5RS, 6SR)-2-(4-acetylphenyl)-6-phenyl-5,6-dihydro-4H-1,3-oxazin-5-ol (2 g) in tetrahydrofuran (25 cc). The solution obtained is heated to 50° C. for 5 hours and then concentrated to dryness under reduced pressure (2.7 kPa). After recrystallization in ethanol, (5RS, 6SR)-2-(4-acetylphenyl)-6-phenyl-5-phenylcarbamoyloxy-5,6-dihydro-4H-1,3-oxazine (1.9 g), m.p. 168° C., is obtained.

(5RS, 6SR)-2-(4-Acetylphenyl)-6-phenyl-5,6-dihydro-4H-1,3-oxazin-5-ol may be prepared in the following manner: a 0.55 M solution (43 cc) of 3-chloroperbenzoic acid in dichloromethane is added dropwise at a temperature in the region of 0° C. to a solution, maintained under an argon atmosphere, of (E)-4-acetyl-N-cinnamylbenzamide (6.6 g) in dichloromethane (60 cc). The suspension obtained is stirred in the region of 0° C. for 5 hours and then filtered. To the filtrate obtained, maintained under an argon atmosphere, boron trifluoride etherate (3 cc) is added dropwise at a temperature in the region of 0° C. The mixture obtained is then stirred for 2 hours at a temperature in the region of 20°

C. and thereafter added to distilled water (100 cc). The organic phase is separated and then washed successively with 1 N aqueous sodium thiosulphate solution (30 cc), distilled water (30 cc) and saturated aqueous sodium bicarbonate solution (30 cc), dried over magnesium sulphate, filtered and then concentrated to dryness under reduced pressure (2.7 kPa) at 40° C. The oil obtained is purified by chromatography on silica (0.063-0.2 mm; 200 g) contained in a column 2.5 cm in diameter, collecting 30-cc fractions. Fractions 45 to 63, eluted with a mixture of cyclohexane and ethyl acetate (1:1 by volume) are concentrated to dryness under reduced pressure (2.7 kPa) at 40° C. After recrystallization in ethyl acetate, (5RS, 6SR)-2-(4-acetylphenyl)-6-phenyl-5,6-dihydro-4H-1,3-oxazin-5-ol (2 g), m.p. 130° C., is obtained.

(E)-4-Acetyl-N-cinnamylbenzamide may be prepared in the following manner: working as in Example 21 for the preparation of (E)-3-chloro-N-cinnamylbenzamide but starting with cinnamylamine (6.65 g) and 4-acetylbenzoic acid (9.02 g), and after recrystallization in ethyl acetate, (E)-4-acetyl-N-cinnamylbenzamide (6.6 g), m.p. 120° C., is thereby obtained.

EXAMPLE 43

Phenyl isocyanate (2.38 g) is added at a temperature in the region of 20° C. to a solution, maintained under an argon atmosphere, of (5RS, 6SR)-2-(4-isopropylphenyl)-6-phenyl-5,6-dihydro-4H-1,3-oxazin-5-ol (6 g) in 1,2-dichloroethane (71 cc). The solution obtained is heated to 80° C. for 3 hours and then concentrated to dryness under reduced pressure (2.7 kPa). The solid obtained is purified by chromatography on silica (0.063-0.2 mm; 300 g) contained in a column 3.5 cm in diameter, collecting 40-cc fractions. Fractions 22 to 27, eluted with a mixture of cyclohexane and ethyl acetate (8:2 by volume), are concentrated to dryness under reduced pressure (2.7 kPa) at 40° C. After recrystallization in a mixture of petroleum ether and ethanol (7:2 by volume), (5RS, 6SR)-2-(4-isopropylphenyl)-6-phenyl-5-phenylcarbamoyloxy-5,6-dihydro-4H-1,3-oxazine (1.6 g), m.p. 144° C., is obtained.

(5RS, 6SR)-2-(4-Isopropylphenyl)-6-phenyl-5,6-dihydro-4H-1,3-oxazin-5-ol may be prepared in the following manner: a 0.39 M solution (56.4 cc) of 3-chloroperbenzoic acid in dichloromethane is added dropwise at a temperature in the region of 0° C. to a solution, maintained under an argon atmosphere, of (E)-4-isopropyl-N-cinnamylbenzamide (5.5 g) in dichloromethane (50 cc). The suspension obtained is stirred at a temperature in the region of 20° C. for 2 hours and then filtered. To the filtrate obtained and maintained under an argon atmosphere, boron trifluoride etherate (2.4 cc) is added dropwise at a temperature in the region of 0° C. The mixture obtained is then stirred for 2 hours at a temperature in the region of 20° C. and thereafter added to distilled water (50 cc). The organic phase is separated and then washed successively with 1 N aqueous sodium thiosulphate solution (30 cc), distilled water (30 cc) and saturated aqueous sodium bicarbonate solution (30 cc), dried over magnesium sulphate, filtered and then concentrated to dryness under reduced pressure (2.7 kPa) at 40° C. The oil thereby obtained is used without further purification.

(E)-4-Isopropyl-N-cinnamylbenzamide may be prepared by working in the following manner: working as in Example 21 for the preparation of (E)-3-chloro-N-cinnamylbenzamide, but starting with cinnamylamine (6.65 g) and 4-isopropylbenzoic acid (9.02 g), and after recrystallization in ethyl acetate, (E)-4-isopropyl-N-cinnamylbenzamide (5.5 g), m.p. 142° C., is obtained.

EXAMPLE 44

By working in a manner similar to that described in Example 38, but starting with (5RS, 6SR)-2-(4-morpholinophenyl)-6-phenyl-5,6-dihydro-4H-1,3-oxazin-5-ol (1.1 g) and phenyl isocyanate (0.46 g), and after purification of the crude product obtained by chromatography on silica (0.063-0.2 mm; 60 g) contained in a column 2.5 cm in diameter, eluting in 20-cc fractions with an ethyl acetate/methanol mixture (95:5 by volume), recovery and concentration under reduced pressure (2.7 kPa) of fractions 4 to 8 followed by recrystallization of the residue thereby obtained in an ethyl acetate/isopropyl ether mixture (50:50 by volume), (5RS, 6SR)-2-(4-morpholinophenyl)-6-phenyl-5-phenylcarbamoyloxy-5,6-dihydro-4H-1,3-oxazine (0.55 g), m.p. 175° C., is obtained.

(5RS, 6SR)-2-(4-Morpholinophenyl)-6-phenyl-5,6-dihydro-4H-1,3-oxazin-5-ol may be prepared in the following manner: working as in Example 38 for the preparation of (5RS, 6SR)-2-[4-(dimethylamino)phenyl]-6-phenyl-5,6-dihydro-4H-1,3-oxazin-5-ol, but starting with N-[(2RS, 3RS)-2,3-epoxy-3-phenylpropyl]-4-morpholinobenzamide (1.6 g) and boron trifluoride etherate (0.65 cc) in dichloromethane (11 cc), and after purification of the crude product by chromatography on silica (0.063-0.2 mm; 80 g) contained in a column 2.5 cm in diameter, eluting in 20-cc fractions with ethyl acetate, recovering and concentration to dryness under reduced pressure (2.7 kPa) of fractions 2 to 41, (5RS, 6SR)-2-(4-morpholinophenyl)-6-phenyl-5,6-dihydro-4H-1,3-oxazin-5-ol (1.1 g) is obtained, and is used without further purification in subsequent syntheses.

N-[(2RS, 3RS)-2,3-Epoxy-3-phenylpropyl]-4-morpholinobenzamide may be prepared in the following manner: working as in Example 38 for the preparation of N-[(2RS, 3RS)-2,3-epoxy-3-phenylpropyl]-4-(dimethylamino)benzamide, but starting with 4-morpholinobenzoic acid (3.44 g), carbonyldiimidazole (2.7 g), N-[(2RS, 3RS)-2,3-epoxy-3-phenylpropyl]trifluoroacetamide (2.72 g), 3.5 N aqueous potassium hydroxide solution (3.2 cc) and dichloromethane (100 cc), and after recrystallization in ethyl acetate N-[(2RS, 3RS)-2,3-epoxy-3-phenylpropyl]-4-morpholinobenzamide (1.9 g), m.p. 150° C., is obtained.

4-Morpholinobenzoic acid may be prepared in the following manner: a mixture of 4-fluorobenzoic acid (21 g) and morpholine (65 cc) is heated to a temperature of 180° C. for 20 hours. After the reaction mixture is cooled, water (100 cc) is added and the pH of the suspension obtained is adjusted to 6 by adding 5 N aqueous hydrochloric acid solution. The insoluble product is separated by filtration and then resuspended in distilled water (100 cc), and the pH of the suspension obtained is adjusted to 11 by adding caustic soda solution.

The aqueous phase is extracted with dichloromethane (2 × 200 cc) and then acidified to pH 6 by adding 5 N aqueous hydrochloric solution, and the insoluble product is separated by filtration. After the product is washed with water and dried, 4-morpholinobenzoic acid (3.5 g) is obtained.

EXAMPLE 45

A mixture of (5RS, 6SR)-2-[4-(trifluoroacetamido)-phenyl]-5,6-dihydro-4H-1,3-oxazin-5-ol (1.8 g) and phenyl isocyanate (0.7 g) in 1,2-dichloroethane (75 cc) is heated to reflux for 6 hours. After being cooled, the reaction mixture is concentrated to dryness under reduced pressure (2.7 kPa) and the residue obtained is purified by chromatography on silica (0.063–0.2 mm; 50 g) contained in a column 2.5 cm in diameter, eluting in 20-cc fractions with an ethyl acetate/cyclohexane mixture (50:50 by volume). Fractions 3 to 7 are combined and concentrated to dryness under reduced pressure (2.7 kPa). The residue obtained is stirred with diisopropyl ether (10 cc) and the insoluble product is separated by filtration and dried in the air. (5RS, 6SR)-6-Phenyl-5-phenylcarbamoyloxy-2-[4-(trifluoroacetamido)-phenyl]-5,6-dihydro-4H-1,3-oxazine (1 g), m.p. 210° C., is thereby obtained.

A mixture of (5RS, 6SR)-6-phenyl-5-phenylcarbamoyloxy-2-[4-(trifluoroacetamido)phenyl]-5,6-dihydro-4H-1,3-oxazine (1 g) and potassium hydroxide pellets (0.3 g) in distilled water (25 cc) is heated to a temperature in the region of 80° C. for 4 hours. After being cooled, the reaction mixture is extracted with dichloromethane (2×50 cc) and the organic solution is dried and concentrated to dryness under reduced pressure (2.7 kPa). The residue obtained is purified by chromatography on silica (20 g) contained in a column 1 cm in diameter and eluting in 10-cc fractions with an ethyl acetate/cyclohexane mixture (50:50 by volume). Fractions 5 to 12 are combined and concentrated to dryness and the residue is dried under reduced pressure (0.1 kPa). (5RS, 6SR)-2-(4-Aminophenyl)-6-phenyl-2-phenylcarbamoyloxy-5,6-dihydro-4H-1,3-oxazin (0.45 g), m.p. 110° C., is thereby obtained.

(5RS, 6SR)-6-Phenyl-2-[4-(trifluoroacetamido)-phenyl]-5,6-dihydro-4H-1,3-oxazin-5-ol may be prepared in the following manner: working as in Example 38 for the preparation of (5RS, 6SR)-2-[4-(dimethylamino)phenyl]-6-phenyl-5,6-dihydro-4H-1,3-oxazin-5-ol, but starting with N-[(2RS, 3RS)-2,3-epoxy-3-phenylpropyl]-4-(trifluoroacetamido)benzamide (3.6 g) and boron trifluoride etherate (1.35 cc) in dichloromethane (75 cc). After treatment of the residue obtained by stirring with isopropyl ether (20 cc), filtration and drying in the air, (5RS, 6SR)-2-[4-(trifluoroacetamido)-phenyl]-6-phenyl-5,6-dihydro-4H-1,3-oxazin-5-ol (1.8 g), m.p. 210° C., is obtained.

N-[(2RS, 3RS)-2,3-Epoxy-3-phenylpropyl]-4-(trifluoroacetamido)benzamide may be prepared in the following manner: working as in Example 38 for the preparation of N-[(2RS, 3RS)-2,3-epoxy-3-phenylpropyl]-4-(dimethylamino)benzamide, but starting with 4-(trifluoroacetamido)benzoic acid (19.2 g), carbonyldiimidazole (13.4 g), N-(2,3-epoxy-3-phenylpropyl)trifluoroacetamide (18 g), 3 N aqueous potassium hydroxide solution (25 cc) and dichloromethane (450 cc), and after purification by chromatography of the residue obtained on silica (0.063–0.2 mm; 500 g) contained in a column 4.5 cm in diameter, eluting in 25-cc fractions with an ethyl acetate/cyclohexane mixture (70:30 by volume), recovery and concentration under reduced pressure (2.7 kPa) of fractions 6 to 14 and recrystallization in diisopropyl ether, N-[(2RS, 3SR)-2,3-epoxy-3-phenylpropyl]-4-(trifluoroacetamido)benzamide (3.7 g), m.p. 190°, is obtained.

4-(Trifluoroacetamido)benzoic acid may be prepared according to the method described by F. WGYGAND and E. LEISING, Chem. Ber., 87, 248 (1954).

EXAMPLE 46

Phenyl isocyanate (2 g) is added at a temperature in the region of 20° C. to a solution, maintained under an argon atmosphere, of (5RS, 6SR)-2-(4-piperidinophenyl)-6-phenyl-5,6-dihydro-4H-1,3-oxazin-5-ol (3.4 g) in tetrahydrofuran (35 cc). The solution obtained is heated to 50° C. for 5 hours and then concentrated to dryness under reduced pressure (2.7 kPa). The solid obtained is purified by chromatography on silica (0.063–0.2 mm; 200 g) contained in a column 2.5 cm in diameter, collecting 30-cc fractions. Fractions 9 to 13, eluted with a mixture of cyclohexane and ethyl acetate (6:4 by volume) are concentrated to dryness under reduced pressure (2.7 kPa) at 40° C. The solid obtained is again purified by chromatography on silica (0.063–0.2 mm; 100 g) contained in a column 2.5 cm in diameter, collecting 15-cc fractions. Fractions 11 to 15, eluted with a mixture of chloroform and methanol (95:5 by volume) are concentrated to dryness under reduced pressure (2.7 kPa) at 40° C. After recrystallization in a mixture of petroleum ether and ethanol (9:1 by volume), (5RS, 6SR)-2-(4-piperidinophenyl)-6-phenyl-5-phenylcarbamoyloxy-5,6-dihydro-4H-1,3-oxazine (1.5 g), m.p. 166° C. is obtained.

(5RS, 6SR)-2-(4-Piperidinophenyl)-6-phenyl-5,6-dihydro-4H-1,3-oxazin-5-ol may be prepared in the following manner: boron trifluoride etherate (4.4 cc), dissolved in dichloromethane (10 cc) is added dropwise at a temperature in the region of 0° C. to a solution, maintained under an argon atmosphere, of N-[(2RS, 3RS)-2,3-epoxy-3-phenylpropyl]-4-piperidinobenzamide (7.6 g) in dichloromethane (100 cc). The solution obtained is then stirred for 30 minutes at a temperature in the region of 20° C. and thereafter treated with 1 N aqueous sodium hydroxide solution (40 cc), stirring being maintained for 30 minutes. The aqueous phase is separated and then re-extracted with ethyl acetate (2×50 cc). The organic phases are combined, dried over magnesium sulphate, filtered and then concentrated to dryness under reduced pressure (2.7 kPa) at 40° C. After recrystallization in a mixture of cyclohexane and ethyl acetate (1:1 by volume), (5RS, 6SR)-2-(4-piperidinophenyl)-6-phenyl-5,6-dihydro-4H-1,3-oxazin-5-ol (3.4 g), m.p. 130° C., is obtained.

N-[(2RS, 3RS)-2,3-Epoxy-3-phenylpropyl]-4-piperidinobenzamide may be prepared in the following manner:

a—Preparation of the solution A:

Carbonyldiimidazole (9 g) is added in small portions at a temperature in the region of 0° C. to a solution (maintained under an argon atmosphere) of 4-piperidinobenzoic acid (11.5 g) in dichloromethane (300 cc). The solution obtained (solution A) is then stirred for 2 hours at a temperature in the region of 20° C. while the solution B is prepared.

b—Preparation of the solution B:

N-[(2RS, 3RS)-2,3-Epoxy-3-phenylpropyl]trifluoroacetamide (9 g) are added to 3 N aqueous potassium hydroxide (12.8 cc). After 7 minutes' stirring at a temperature in the region of 20° C., the solution obtained is saturated with sodium chloride and then extracted with dichloromethane (2×100 cc). The organic phases are combined, dried over magnesium sulphate and then filtered, thereby forming a methylene chloride solution of (2RS, 3RS)-2,3-epoxy-3-phenylpropanamine (solution B).

The solution B is added dropwise to the solution A. The solution obtained is then stirred for 3 hours at a temperature in the region of 20° C. and thereafter poured into distilled water (100 cc). The aqueous phase is separated and then re-extracted with dichloromethane (2×50 cc). The organic phases are combined, washed with saturated aqueous sodium chloride solution, dried over magnesium sulphate, filtered and then concentrated to dryness under reduced pressure (2.7 kPa) at 40° C. After recrystallization in a mixture of ethyl acetate and diisopropyl ether (1:1 by volume), N-[(2RS, 3RS)-2,3-epoxy-3-phenylpropyl]-4-piperidinobenzamide (7.6 g) is obtained.

4-Piperidinobenzoic acid may be prepared in the following manner: a mixture of 4-fluorobenzoic acid (21 g) and piperidine (75 cc) is heated with stirring in an autoclave for 17 hours at a temperature of 180° C., then cooled to a temperature in the region of 20° C. and poured into distilled water (750 cc). After acidification to pH 6-7 with 5 N aqueous hydrochloric acid solution, the solid formed is separated by filtration. After recrystallization in acetonitrile, 4-piperidinobenzoic acid (11.5 g), m.p. 230° C., is obtained.

EXAMPLE 47

A mixture of (5RS, 6SR)-2-[4-(N-methyltrifluoroacetamido)phenyl]-6-phenyl-5,6-dihydro-4H-1,3-oxazin-5-ol (1.54 g) and phenyl isocyanate (0.6 g) in 1,2-dichloroethane (25 cc) is heated to reflux for 18 hours. The reaction mixture is then concentrated to dryness under reduced pressure (2.7 kPa). After recrystallization of the residue thereby obtained in isopropyl ether, (5RS, 6SR)-2-[4-(N-methyltrifluoroacetamido)-phenyl]-6-phenyl-5-phenylcarbamoyloxy-5,6-dihydro-4H-1,3-oxazine (0.77 g), m.p. 160° C., is obtained.

A mixture of (5RS, 6SR)-2-[4-(N-methyltrifluoroacetamido)phenyl]-6-phenyl-5-phenylcarbamoyloxy-5,6-dihydro-4H-1,3-oxazine (0.57 g) and potassium hydroxide pellets (0.15 g) in water (9 cc) is heated to reflux for 18 hours. After being cooled, the reaction mixture is extracted with dichloromethane (2×20 cc) and the organic solution is then dried and concentrated to dryness under reduced pressure (2.7 kPa). The residue obtained is purified by chromatography on silica (0.063–0.2 mm; 30 g) contained in a column 2.5 cm in diameter, eluting in 20-cc fractions with an ethyl acetate/cyclohexane mixture (30:70 by volume). Fractions 7 to 20 are combined and concentrated to dryness under reduced pressure (2.7 kPa). (5RS, 6SR)-2-[4-(Methylamino)phenyl]-6-phenyl-5-phenylcarbamoyloxy-5,6-dihydro-4H-1,3-oxazine (0.18 g), m.p. 170 C., is thereby obtained.

(5RS, 6SR)-2-[4-(N-Methyltrifluoroacetamido)-phenyl]-6-phenyl-5,6-dihydro-4H-1,3-oxazin-5-ol may be prepared in the following manner: working as in Example 38 for the preparation of (5RS, 6SR)-2-[4-(dimethylamino)phenyl]-6-phenyl-5,6-dihydro-4H-1,3-oxazin-5-ol, but starting with N-[(2RS, 3RS)-2,3-epoxy-3-phenylpropyl]-4-(N-methyltrifluoroacetamido)benzamide (2.13 g) and boron trifluoride etherate (0.75 cc) in dichloromethane (15 cc), and after chromatography of the product obtained on silica (0.063–02 mm; 150 g) contained in a column 3.5 cm in diameter, eluting in 30-cc fractions with an ethyl acetate/cyclohexane mixture (80:20 by volume), recovery and concentration under reduced pressure (2.7 kPa) of fractions 11 to 20, (5RS, 6SR)-2-[4-(N-methyltrifluoroacetamido)phenyl]-6-phenyl-5,6-dihydro-4H-1,3-oxazin-5-ol (1.5 g) is obtained in the form of an oil, which is used without further purification in the subsequent phases.

N-[(2RS, 3RS)-2,3-Epoxy-3-phenylpropyl]-4-(N-methyltrifluoroacetamido)benzamide may be prepared in the following manner: working as in Example 38 for the preparation of N-[(2RS, 3RS)-2,3-epoxy-3-phenylpropyl]-4-dimethylamino)benzamide, but starting with 4-(N-methyltrifluoroacetamido)benzoic acid (8 g), carbonyldiimidazole (5.25 g), N-(2,3-epoxy-3-phenylpropyl)trifluoroacetamide (5.22 g), 3.5 N aqueous potassium hydroxide solution (6 cc) and dichloromethane (160 cc), and after chromatography of the residue obtained on silica (0.063–0.2 mm; 400 g) contained in a column 4.5 cm in diameter, eluting in 50-cc fractions with an ethyl acetate/cyclohexane mixture (80:20 by volume), recovering and concentration under reduced pressure of fractions 14 to 20, N-[(2RS, 3RS)-2,3-epoxy-3-phenylpropyl]-4-N-methyltrifluoroacetamido)benzamide (2.1 g) is obtained in the form of a yellow oil, which is used without further purification in the subsequent phases.

4-(N-Methyltrifluoroacetamido)benzoic acid may be prepared in the following manner: a solution of trifluoroacetic anhydride (43.75 g) in anhydrous diethyl ether (50 cc) is added to a solution of 4-methylaminobenzoic acid (21 g) in anhydrous diethyl ether (200 cc) while the temperature is maintained in the vicinity of 0° C. The reaction mixture is then stirred for 20 hours at a temperature in the region of 20° C. and is thereafter concentrated to dryness under reduced pressure (2.7 kPa). On recrystallization of the residue obtained in a diisopropyl ether/ethyl acetate mixture (80:20 by volume), 4-(N-methyltrifluoroacetamido)benzoic acid (7.5 g), m.p. 175° C., is obtained.

EXAMPLE 48

A mixture of (5RS, 6RS)-6-phenyl-2-[4-(trifluoromethoxy)phenyl]-5,6-dihydro-4H-1,3-oxazin-5-ol (6 g) and phenyl isocyanate (2.4 g) in 1,2-dichloroethane (100 cc) is heated to a temperature in the region of 60° C. for 5 hours. After being cooled, the reaction mixture is concentrated to dryness under reduced pressure (2.7 kPa) and the residue obtained is purified by chromatography on silica (0.063–0.2 mm; 200 g) contained in a column 3.5 cm in diameter, eluting in 20-cc fractions with an ethyl acetate/cyclohexane mixture (30:70 by volume). Fractions 4 to 8 are combined and concentrated to dryness under reduced pressure (2.7 kPa). The residue is crystallized in diisopropyl ether (5 cc). (5RS, 6SR)-6-Phenyl-5-phenylcarbamoyloxy-2-[4-(trifluoromethoxy)phenyl]-5,6-dihydro-4H-1,3-oxazine (1.1 g), m.p. 128° C., is thereby obtained.

(5RS, 6SR)-6-Phenyl-2-[4-(trifluoromethoxy)-phenyl]-5,6-dihydro-4H-1,3-oxazin-5-ol may be prepared in the following manner: working as in Example 12 for the preparation of (5RS, 6SR)-2,6-diphenyl-5,6-dihydro-4H-1,3-oxazin-5-ol, but starting with (E)-N-cinnamyl-4-(trifluoromethoxy)benzamide (13 g), a 0.44 M meta-chloroperbenzoic acid solution (95 cc), boron trifluoride etherate (5.4 cc) and dichloromethane (150 cc), and after chromatography of the product obtained on silica (0.063–0.2 mm; 200 g) contained in a column 3.5 cm in diameter, eluting in 25-cc fractions with an ethyl acetate/cyclohexane mixture (40–60 by volume), recovery and concentration under reduced pressure (2.7 kPa) of the fractions 8 to 14, (5RS, 6SR)-6-phenyl-2-[4-(trifluoromethoxy)phenyl]-5,6-dihydro-4H-1,3-oxazin-5-ol (6.4 g), m.p. 120° C., is obtained.

(E)-N-Cinnamyl-4-(trifluoromethoxy)benzamide may be prepared in the following manner: working as in Example 19 for the preparation of (E)-N-cinnamyl-4-methoxybenzamide, but starting with 4-(trifluoromethoxy)benzoic acid (11.6 g), oxalyl dichloride (5.3 cc), (E)-cinnamylamine (7.4 g), triethylamine (16 cc), dimethylformamide (0.2 cc), diethyl ether (100 cc) and dichloromethane (150 cc), and recrystallization in diisopropyl ether, (E)-N-cinnamyl-4-(trifluoromethoxy)benzamide (13 g), m.p. 136° C., is obtained.

EXAMPLE 49

A mixture of (5RS, 6SR)-2-[4-(ethylthio)phenyl]-6-phenyl-5,6-dihydro-4H-1,3-oxazin-5-ol (6.5 g) and phenylisocyanate (2.6 g) in 1,2-dichloroethane (100 cc) is heated to a temperature in the region of 80° C. for 5 hours. After being cooled, the reaction mixture is concentrated to dryness under reduced pressure (2.7 kPa) and the residue obtained is purified by chromatography on silica (0.063-0.2 mm; 150 g) contained in a column 3.5 cm in diameter eluting in 20-cc fractions with an ethylacetate/cyclohexane mixture (50:50 by volume). Fractions 5 to 15 are combined and concentrated to dryness under reduced pressure (2.7 kPa). The residue obtained is further purified by chromatography on silica (0.063-0.2 mm; 100 g) contained in a column 3.5 cm in diameter, eluting in 25-cc fractions with a methylene chloride/methanol mixture (99:1 by volume). Fractions 10 to 18 are combined and concentrated to dryness under reduced pressure. (5RS, 6SR)-2-[4-(Ethylthio)phenyl]-6-phenyl-5-phenylcarbamoyloxy-5,6-dihydro-4H-1,3-oxazine (1.1 g), m.p. 70° C., is thereby obtained.

(5RS, 6SR)-2-[4-(Ethylthio)phenyl]-6-phenyl-5,6-dihydro-4H-1,3-oxazin-5-ol may be prepared in the following manner: working as in Example 38 for the preparation of 2-[4-(dimethylamino)phenyl]-6-phenyl-5,6-dihydro-4H-1,3-oxazin-5-ol, but starting with N-[(2RS, 3RS)-2,3-epoxy-3-phenylpropyl]-4-(ethylthio)benzamide (10 g) and boron trifluoride etherate (4.3 cc) in dichloromethane (100 cc), and after crystallization of the residue obtained in an ethyl acetate/diisopropyl ether mixture (30:70 by volume), (5RS, 6SR)-2-[4-(ethylthio)phenyl]-6-phenyl-5,6-dihydro-4H-1,3-oxazin-5-ol (4.2 g), m.p. 120° C., is obtained.

N-(2,3-epoxy-3-phenylpropyl)-4-(ethylthio)benzamide may be prepared in the following manner: working as in Example 38 for the preparation of N-[(2RS, 3RS)-2,3-epoxy-3-propyl]dimethylaminobenzamide, but starting with 4-(ethylthio)benzoic acid (13.6 g), carbonyldiimidazole (12 g), N-(2,3-epoxy-3-phenylpropyl)trifluoroacetamide (12.25 g), 3.2 N aqueous potassium hydroxide solution (16 cc) and dichloromethane (375 cc), and after treatment of the residue obtained by chromatography on silica (0.063-0.2 mm; 400 g) contained in a column 4.5 cm in diameter, eluting in 25-cc fractions with an ethyl acetate/cyclohexane mixture (50:50 by volume), recovery and concentration to dryness under reduced pressure (2.7 kPa) of fractions 2 to 5, N-[(2RS, 3RS)-2,3-epoxy-3-phenylpropyl]-4-(ethylthio)benzamide (10 g) is obtained in the form of a yellow oil, which is used without further purification in the subsequent syntheses.

EXAMPLE 50

Phenyl isocyanate (2 g) is added at a temperature in the region of 20° C. to a solution, maintained under an argon atmosphere, of (5RS, 6SR)-2-(4-tert-butylphenyl)-6-phenyl-5,6-dihydro-4H-1,3-oxazin-5-ol (3.2 g) in anhydrous tetrahydrofuran (35 cc). The solution obtained is heated to 50° C. for 5 hours and then concentrated to dryness under reduced pressure (2.7 kPa). The solid obtained is purified by chromatography on silica (0.063-0.2 mm; 200 g) contained in a column 3.5 cm in diameter, collecting 20-cc fractions. Fractions 22 to 29, eluted with a mixture of cyclohexane and ethyl acetate (7:3 by volume), are concentrated to dryness under reduced pressure (2.7 kPa) at 40° C. The solid obtained is again purified by chromatography on silica (0.063-0.2 mm; 200 g) contained in a column 2.5 cm in diameter, collecting 10-cc fractions. Fractions 19 to 25, eluted with a mixture of dichloromethane and methanol (98:2 by volume), are concentrated to dryness under reduced pressure (2.7 kPa) at 40° C. After recrystallization in ethyl acetate, (5RS, 6SR)-2-(4-tert-butylphenyl)-6-phenyl-5-phenylcarbamoyloxy-5,6-dihydro-4H-1,3-oxazine (1.4 g), m.p. 80° C., is obtained.

(5RS, 6SR)-2-(4-tert-Butylphenyl)-6-phenyl-5,6-dihydro-4H-1,3-oxazin-5-ol may be prepared in the following manner: a 0.38 M solution (94.7 cc) of 3-chloroperbenzoic acid in dichloromethane is added dropwise at a temperature in the region of 0° C. to a solution, maintained under an argon atmosphere, of (E)-4-tert-butyl-N-cinnamylbenzamide (8.9 g) in dichloromethane (80 cc). The suspension obtained is stirred at a temperature in the region of 20° C. for 2 hours and then filtered. To the filtrate obtained, maintained under an argon atmosphere, boron trifluoride etherate (3.8 cc) is added dropwise at a temperature in the region of 0° C. The mixture obtained is then stirred for 2 hours at a temperature in the region of 20° C. and thereafter added to distilled water (50 cc). The organic phase is separated and then washed successively with 1 N aqueous sodium thiosulphate solution (30 cc), distilled water (30 cc) and saturated aqueous sodium bicarbonate solution (30 cc), dried over magnesium sulphate, filtered and then concentrated to dryness under reduced pressure (2.7 kPa) at 40° C. The oil obtained is purified by chromatography on silica (0.063-0.2 mm; 200 g) contained in a column 3.5 cm in diameter, collecting 20-cc fractions. Fractions 50 to 90, eluted with a mixture of cyclohexane and ethyl acetate (7:3 by volume), are concentrated to dryness under reduced pressure (2.7 kPa) at 40° C. After recrystallization in ethyl acetate, (5RS, 6SR)-2-(4-tert-butylphenyl)-6-phenyl-5,6-dihydro-4H-1,3-oxazin-5-ol (0.8 g), m.p. 50° C., is obtained.

(E)-4-tert-Butyl-N-cinnamylbenzamide may be prepared in the following manner: working in a manner similar to that described in Example 21 for the preparation of (E)-3-chloro-N-cinnamylbenzamide, but starting with cinnamylamine (6.65 g) and 4-tert-butylbenzoic acid (9.8 g). After recrystallization in ethyl acetate, (E)-4-tert-butyl-N-cinnamylbenzamide (8.9 g) is thereby obtained.

EXAMPLE 51

3-Aminophenol (1 g) is added at a temperature in the region of 20° C. to a solution, maintained under an argon atmosphere, of (5RS, 6SR)-5-(4-nitrophenoxycarbonyloxy)-2,6-diphenyl-5,6-dihydro-4H-1,3-oxazine (2.5 g) in anhydrous dimethylformamide (30 cc). The solution obtained is heated at 70° C. for 5 hours, then cooled to a temperature in the region of 20° C. and poured into distilled water (300 cc). The mixture is extracted with dichloromethane (2×150 cc). The organic phases are combined, washed with distilled water (3×20 cc), dried over magnesium sulphate and concentrated to dryness under reduced pressure (2.7 kPa) at 40° C. The oil obtained is purified by chromatography on silica (0.063–0.2 mm; 100 g) contained in a column 2 cm in diameter [eluent: cyclohexane/ethyl acetate/triethylamine (60:35:5 by volume)], collecting 25-cc fractions. The fractions 10 to 17 are combined and concentrated to dryness under reduced pressure (2.7 kPa) at 40° C. After recrystallization in diisopropyl ether, (5RS, 6SR)-5-(3-hydroxyphenylcarbamoyloxy)-2,6-diphenyl-5,6-dihydro-4H-1,3-oxazine (1.1 g), m.p. 170° C., is obtained.

EXAMPLE 52

A solution of (4RS, 5RS)-2-(4-methoxyphenyl)-4-phenyl-5,6-dihydro-4H-1,3-oxazin-5-ol (1.42 g) in anhydrous tetrahydrofuran (15 cc) is added at a temperature in the region of 20° C. to an oily suspension (50% by weight; 0.27 g), maintained under an argon atmosphere, of sodium hydride in anhydrous tetrahydrofuran (15 cc), and the solution obtained is stirred for 30 minutes at this same temperature. A solution of 3,4-dichlorophenyl isocyanate (1.05 g) in anhydrous tetrahydrofuran (10 cc) is then added dropwise and stirring is continued for 4 hours at a temperature in the region of 20° C. Distilled water (20 cc) is then added and the mixture is extracted with dichloromethane (3×80 cc). The organic phases are combined, washed with distilled water (3×20 cc), dried over magnesium sulphate and concentrated to dryness under reduced pressure (2.7 kPa) at 40° C. The solid obtained is purified by chromatography on silica (0.063–0.2 mm; 300 g) contained in a column 3.5 cm in diameter (eluent: dichloromethane), collecting 30 cc fractions. Fractions 4 to 7 are combined and concentrated to dryness under reduced pressure (2.7 kPa) at 40° C. The solid obtained is again purified by chromatography on silica (0.063–0.2 mm; 125 g) contained in a column 2 cm in diameter [eluent: cyclohexane/ethyl acetate (6:4 by volume)], collecting 20-cc fractions. The fractions 5 to 9 are combined and concentrated to dryness under reduced pressure (2.7 kPa) at 40° C. After recrystallization in diisopropyl ether, (4RS, 5RS)-5-(3,4-dichlorophenylcarbamoyloxy)-2-(4-methoxyphenyl)-4-phenyl-5,6-dihydro-4H-1,3-oxazine (1.1 g), m.p. 130° C., is obtained.

EXAMPLE 53

Phenyl isocyanate (0.7 g) is added at a temperature in the region of 20° C. to a solution, maintained under an argon atmosphere, of (5RS, 6SR)-2-(2-naphthyl)-6-phenyl-5,6-dihydro-4H-1,3-oxazin-5-ol (1.8 g) in 1,2-dichloroethane (21 cc). The solution obtained is heated to 80° C. for 4 hours and then concentrated to dryness under reduced pressure (2.7 kPa). The solid obtained is purified by chromatography on silica (0.063–0.2 mm; 200 g) contained in a column 2.5 cm in diameter, collecting 20-cc fractions. The fractions 12 to 20, eluted with dichloromethane, are concentrated to dryness under reduced pressure (2.7 kPa) at 40° C. After recrystallization in acetonitrile, (5RS, 6SR)-2-(2-naphthyl)-6-phenyl-5-phenylcarbamoyloxy-5,6-dihydro-4H-1,3-oxazine (0.9 g), m.p. 163° C., is obtained.

(5RS, 6SR)-2-(2-Naphthyl)-6-phenyl-5,6- dihydro-4H-1,3-oxazin-5-ol may be prepared in the following manner: a 0.38 M solution (49 cc) of 3-chloroperbenzoic acid in dichloromethane is added dropwise at a temperature in the region of 0° C. to a solution, maintained under an argon atmosphere, of (E)-N-cinnamyl-2-naphthalenecarboxamide (4.3 g) in dichloromethane (40 cc).

The suspension obtained is stirred at a temperature in the region of 20° C. for 3 hours and then filtered. To the filtrate obtained, maintained under an argon atmosphere, boron trifluoride etherate (1.9 cc) is added dropwise at a temperature in the region of 0° C. The mixture obtained is then stirred for 2 hours at a temperature in the region of 20° C. and thereafter added to distilled water (50 cc). The organic phase is separated and then washed successively with 1 N aqueous sodium thiosulphate solution (30 cc), distilled water (30 cc) and saturated sodium bicarbonate solution (30 cc), dried over magnesium sulphate, filtered and then concentrated to dryness under reduced pressure (2.7 kPa) at 40 C. After recrystallization in acetonitrile, (5RS, 6SR)-2-(2-naphthyl)-6-phenyl-5,6-dihydro-4H-1,3-oxazin-5-ol (1.8 g), m.p. 172° C., is obtained.

(E)-N-Cinnamyl-2-naphthalenecarboxamide may be obtained in the following manner: working in a manner similar to that described in Example 21 for the preparation of (E)-3-chloro-N-cinnamylbenzamide, starting with cinnamylamine (5.3 g) and 2-naphthoic acid (7.6 g), and after recrystallization in ethyl acetate, (E)-N-cinnamyl-2-naphthalenecarboxamide (4.3 g) is obtained.

The present invention also provides pharmaceutical compositions comprising at least one compound of the formula (I), in association with a pharmaceutically acceptable carrier or coating, which can be inert or physiologically active. The compounds of the invention may be administered orally, parenterally, rectally or topically.

As solid compositions for oral administration, tablets, pills, powders (gelatin capsules, wafer tablets) or granules may be used. In these compositions, the active principle according to the invention is mixed with one or more inert diluents such as starch, cellulose, sucrose, lactose or silica. These compositions can also comprise substances other than diluents, e.g. one or more lubricants such as magnesium stearate or talc, a colorant, a coating (dragees) or a varnish.

As liquid compositions for oral administration, it is possible to use solutions, suspensions, emulsions, syrups and elixirs which are pharmaceutically acceptable, containing inert diluents such as water, ethanol, glycerol, vegetable oils or liquid paraffin. These compositions can comprise substances other than diluents, e.g. wetting, sweetening, thickening, flavouring or stabilizing products.

The sterile compositions for parenteral administration can preferably be suspensions, emulsions or non-aqueous solutions. As a solvent or vehicle, it is possible to employ water, propylene glycol, a polyethylene glycol, vegetable oils, especially olive oil, injectable organic esters, e.g. ethyl oleate, or other suitable organic solvents. These compositions can also contain adjuvants, especially wetting, isotonicity-regulating, emulsifying, dispersing and stabilizing agents.

The sterilization may be carried out in several ways, e.g. by aseptic filtration, by incorporating sterilizing agents in the composition, by irradiation or by heating. They can also be prepared in the form of sterile solid compositions which can be dissolved at the time of use in an injectable sterile medium.

The compositions for rectal administration are suppositories or rectal capsules, which contain, apart from the active product, excipients such as cocoa butter, semisynthetic glycerides or polyethylene glycols.

The compositions for topical administration can be, e.g. creams, ointments, lotions, eye-washes, mouth-washes, nasal drops or aerosols.

In human therapy, the compounds according to the invention are especially useful for the treatment and prevention of disorders involving the action of CCK on the nervous system or the gastrointestinal system. The new compounds can hence be used in the treatment and prevention of psychoses, Parkinson's disease, tardive dyskinesia, irritable colon syndrome, acute pancreatitis, ulcers and disorders of intestinal motility, as potentiators of the analgesic activity of narcotic and non-narcotic analgesic drugs, and as appetite regulators.

The dose used depends on the effect sought, the treatment period and the administration route used; a suitable dose is generally between 0.05 g and 1 g per day orally for an adult, with unit doses ranging from 10 mg to 500 mg of active substance. Generally speaking, the medical practitioner will determine the appropriate dosage in accordance with the age and weight and all other factors specific to the subject to be treated.

The Examples which follow illustrate compositions according to the invention:

EXAMPLE A

Gelatin capsules containing 50 mg of active product and having the following composition are prepared according to the usual technique:

| | |
|---|---|
| (4RS, 5RS)-2-(4-chlorophenyl)-4-phenyl-5-phenylcarbamoyloxy-5,6-dihydro-4H-1,3-oxazine | 50 mg |
| cellulose | 18 mg |
| lactose | 55 mg |
| colloidal silica | 1 mg |
| sodium carboxymethyl starch | 10 mg |
| talc | 10 mg |
| magnesium stearate | 1 mg |

EXAMPLE B

Tablets containing 50 mg of active product and having the following composition are prepared according to the usual technique:

| | |
|---|---|
| (4RS, 5RS)-2-(3,4-methylenedioxyphenyl)-4-phenyl-5-phenylcarbamoyloxy-5,6-dihydro-4H-1,3-oxazine | 50 mg |
| lactose | 104 mg |
| cellulose | 40 mg |
| polyvidone | 10 mg |
| sodium carboxymethyl starch | 22 mg |
| talc | 10 mg |
| magnesium stearate | 2 mg |
| colloidal silica | 2 mg |
| mixture of hydroxymethylcellulose, glycerine and titanium oxide (72:3.5:24.5) q.s. | 1 finished 245 mg film-coated tablet |

EXAMPLE C

An injectable solution containing 10 mg of active product and having the following composition is prepared:

| | |
|---|---|
| (5RS, 6RS)-2-(4-methoxyphenyl)-6-phenyl-5-phenylcarbamoyloxy-5,6-dihydro-4H-1,3-oxazine | 10 mg |
| benzoic acid | 80 mg |
| benzyl alcohol | 0.06 cc |
| sodium benzoate | 80 mg |

| -continued | |
|---|---|
| ethanol, 95% | 0.4 cc |
| sodium hydroxide | 24 mg |
| propylene glycol | 1.6 cc |
| water q.s | 4 cc |

We claim:
1. A compound of formula:

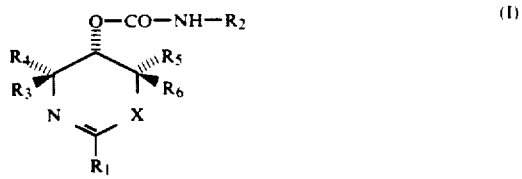

in which

R₁ denotes 2-indolyl, 2-thienyl, 3-furyl, naphthyl, phenyl or phenyl substituted by one or two halogen atoms, or by alkoxy, alkyl, nitro, acylamino, alkylthio, acyl, trifluoromethoxy, morpholino, piperidino, amino, monoalkylamino, or dialkylamino in which the alkyl groups are identical or different, or, at the 3- and 4-positions, by methylenedioxy, R₂ denotes phenyl or phenyl substituted by one or two halogen atoms, by one or two alkyl radicals, or by alkoxy, nitro, trifluoromethyl or hydroxy or, at the 3- and 4-positions, by methylenedioxy, and either X denotes oxygen and R₃ denotes phenyl and R₄, R₅ and R₆ denote hydrogen, or R₃ and R₄ denote hydrogen, R₅ denotes hydrogen or methyl and R₆ denotes phenyl, or one of R₃ and R₄ denotes methyl and the other hydrogen, R₅ denotes hydrogen and R₆ denotes phenyl, or X denotes sulphur, R₃ denotes phenyl and R₄, R₅ and R₆ denote hydrogen; the aforesaid acyl, alkyl and alkoxy radicals and acyl, alkyl and alkoxy portions containing 1 to 4 carbon atoms each in a straight or branched chain, and its acid addition salts.

2. A compound according to claim 1 in which R₁ denotes 2-thienyl, naphthyl, phenyl, or phenyl substituted by one or two halogen atoms, or by alkoxy, alkyl, nitro, acyl, alkylthio, trifluoromethoxy, morpholino, piperidino, amino, monoalkylamino, or dialkylamino in which the alkyl groups are identical or different, or, at the 3- and 4-positions, by methylenedioxy, R₂ denotes phenyl or phenyl substituted by one or two halogen atoms, or by alkyl, alkoxy, nitro, hydroxy or trifluoromethyl or, at the 3- and 4-positions, by methylenedioxy, X denotes oxygen, and R₃, R₄, R₅ and R₆ are as defined in claim 1, the aforesaid acyl, alkyl and alkoxy radicals and the acyl, alkyl and alkoxy portions containing 1 to 4 carbon atoms each in a straight or branched chain, and its acid addition salts.

3. A compound according to claim 1 which is (4RS, 5RS)-2-(4-chlorophenyl)-4-phenyl-5-phenylcarbamoyloxy-5,6-dihydro-4H-1,3-oxazine and its acid addition salts.

4. A compound according to claim 1 which is (4RS, 5RS)-2-(3,4-methylenedioxyphenyl)-4-phenyl-5-phenylcarbamoyloxy-5,6-dihydro-4H-1,3-oxazine and its acid addition salts.

5. A compound according to claim 1 which is (4RS, 5RS)-2-(4-methoxyphenyl)-4-phenyl-5-phenylcarbamoyloxy-5,6-dihydro-4H-1,3-oxazine and its acid addition salts.

6. A compound according to claim 1 which is (5RS, 6SR)-2,6-diphenyl-5-phenylcarbamoyloxy-5,6-dihydro-4H-1,3-oxazine and its acid addition salts.

7. A compound according to claim 1 which is (5RS, 6SR)-5-(3-chlorophenylcarbamoyloxy)-2,6-diphenyl-5,6-dihydro-4H-1,3-oxazine and its acid addition salts.

8. A compound according to claim 1 which is (5RS, 6SR)-5-(3-methylphenylcarbamoyloxy)-2,6-diphenyl-5,6-dihydro-4H-1,3-oxazine and its acid addition salts.

9. A compound according to claim 1 which is (5RS, 6SR)-2-[4-(dimethylamino)phenyl]-6-phenyl-5-phenylcarbamoyloxy-5,6-dihydro-4H-1,3-oxazine and its acid addition salts.

10. A compound according to claim 1 which is (5RS, 6SR)-2-[4-(methylamino)phenyl]-6-phenyl-5-phenylcarbamoyloxy-5,6-dihydro-4H-1,3-oxazine and its acid addition salts.

11. A compound according to claim 1 which is (5RS, 6SR)-2-[4-(ethylthio)phenyl]-6-phenyl-5-phenylcarbamoyloxy-5,6-dihydro-4H-1,3-oxazine and its acid addition salts.

12. A compound according to claim 1 which is (5RS, 6SR)-5-(3-hydroxyphenylcarbamoyloxy)-2,6-diphenyl-5,6-dihydro-4H-1,3-oxazine and its acid addition salts.

13. A compound according to claim 1 which is (5RS, 6SR)-2-(4-methoxyphenyl)-6-phenyl-5-phenylcarbamoyloxy-5,6-dihydro-4H-1,3-oxazine and its acid addition salts.

14. A compound according to claim 1 which is (5RS, 6SR)-2-(4-chlorophenyl)-6-phenyl-5-phenylcarbamoyloxy-5,6-dihydro-4H-1,3-oxazine and its acid addition salts.

15. A compound according to claim 1 which is (5RS, 6SR)-2-(2-fluorophenyl)-6-phenyl-5-phenylcarbamoyloxy-5,6-dihydro-4H-1,3-oxazine and its acid addition salts.

16. A compound according to claim 1 which is (5RS, 6SR)-2-(3,4-dichlorophenyl)-6-phenyl-5-phenylcarbamoyloxy-5,6-dihydro-4H-1,3-oxazine and its acid addition salts.

17. A compound according to claim 1 which is (5RS, 6SR)-2-(4-fluorophenyl)-6-phenyl-5-phenylcarbamoyloxy-5,6-dihydro-4H-1,3-oxazine and its acid addition salts.

18. A compound according to claim 1 which is (4RS, 5RS)-5-(3,4-dichlorophenylcarbamoyloxy)-2,4-diphenyl-5,6-dihydro-4H-1,3-oxazine and its acid addition salts.

19. A compound according to claim 1 which is (5RS, 6SR)-6-phenyl-5-phenylcarbamoyloxy-2-(2-thienyl)-5,6-dihydro-4H-1,3-oxazine and its acid addition salts.

20. A compound according to claim 1 which is (4RS, 5RS)-5-(3,4-methylenedioxyphenylcarbamoyloxy)-2,4-diphenyl-5,6-dihydro-4H-1,3-oxazine and its acid addition salts.

21. A compound according to claim 1 which is (5RS, 6SR)-5-(3-methoxyphenylcarbamoyloxy)-2,6-diphenyl-5,6-dihydro-4H-1,3-oxazine and its acid addition salts.

22. A compound according to claim 1 which is (5RS, 6RS)-5-(3-nitrophenylcarbamoyloxy)-2,6-diphenyl-5,6-dihydro-4H-1,3-oxazine and its acid addition salts.

23. A compound according to claim 1 which is (5RS, 6SR)-6-methyl-2,6-diphenyl-5-phenylcarbamoyloxy-5,6-dihydro-4H-1,3-oxazine and its acid addition salts.

24. A compound according to claim 1 which is (5RS, 6SR)-2-(4-acetylphenyl)-6-phenyl-5-phenylcarbamoyloxy-5,6-dihydro-4H-1,3-oxazine and its acid addition salts.

25. A compound according to claim 1 which is (5RS, 6SR)-2-(4-isopropylphenyl)-6-phenyl-5-phenylcarbamoyloxy-5,6-dihydro-4H-1,3-oxazine and its acid addition salts.

26. A compound according to claim 1 which is (5RS, 6SR)-2-(4-morpholinophenyl)-6-phenyl-5-phenylcarbamoyloxy-5,6-dihydro-4H-1,3-oxazine and its acid addition salts.

27. A compound according to claim 1 which is (5RS, 6SR)-2-(4-piperidinophenyl)-6-phenyl-5-phenylcarbamoyloxy-5,6-dihydro-4H-1,3oxazine and its acid addition salts.

28. A pharmaceutical composition comprising, as active principle, at least one compound of formula:

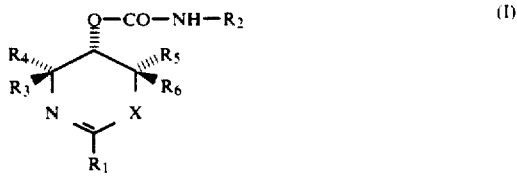

in which $R_1$ denotes 2-indolyl, 2-thienyl, 3-furyl, naphthyl, phenyl or phenyl substituted by one or two halogen atoms, or by alkoxy, alkyl, nitro, acylamino, alkylthio, acyl, trifluoromethoxy, morpholino, piperidino, amino, monoalkylamino, or dialkylamino in which the alkyl groups are identical or different, or, at the 3- and 4-positions, by methylenedioxy, $R_2$ denotes phenyl or phenyl substituted by one or two halogen atoms, by one or two alkyl radicals, or by alkoxy, nitro, trifluoromethyl or hydroxy or, at the 3- and 4-positions, by methylenedioxy, and either X denotes oxygen and $R_3$ denotes phenyl and $R_4$, $R_5$ and $R_6$ denote hydrogen, or $R_3$ and $R_4$ denote hydrogen, $R_5$ denotes hydrogen or methyl and $R_6$ denotes phenyl, or one of the $R_3$ and $R_4$ denotes methyl and the other hydrogen, $R_5$ denotes hydrogen and $R_6$ denotes phenyl, or X denotes sulphur, $R_3$ denotes phenyl and $R_4$, $R_5$ and $R_6$ denote hydrogen; the aforesaid acyl, alkyl and alkoxy radicals and acyl, alkyl and alkoxy portions containing 1 to 4 carbon atoms each in a straight or branched chain, and its acid addition salts, in association with a pharmaceutical carrier or coating.

* * * * *